United States Patent
Dooley et al.

(10) Patent No.: US 10,398,277 B2
(45) Date of Patent: *Sep. 3, 2019

(54) FLOOR CLEANING ROBOT

(71) Applicant: iRobot Corporation, Bedford, MA (US)

(72) Inventors: Michael J. Dooley, Pasadena, CA (US);
Nikolai Romanov, Oak Park, CA (US);
Marcus Williams, Newton, MA (US);
Joseph M. Johnson, Norwood, MA (US)

(73) Assignee: iRobot Corporation, Bedford, MA (US)

(*) Notice: Subject to any disclaimer, the term of this patent is extended or adjusted under 35 U.S.C. 154(b) by 410 days.

This patent is subject to a terminal disclaimer.

(21) Appl. No.: 15/147,661

(22) Filed: May 5, 2016

(65) Prior Publication Data

US 2016/0242613 A1    Aug. 25, 2016

Related U.S. Application Data

(63) Continuation of application No. 14/538,349, filed on Nov. 11, 2014, now Pat. No. 9,615,712, which is a (Continued)

(51) Int. Cl.
*A47L 11/28* (2006.01)
*A47L 11/40* (2006.01)
(Continued)

(52) U.S. Cl.
CPC .......... *A47L 11/4011* (2013.01); *A47L 11/12* (2013.01); *A47L 11/125* (2013.01); *A47L 11/284* (2013.01);
(Continued)

(58) Field of Classification Search
CPC ...... A47L 11/03; A47L 11/065; A47L 11/125; A47L 11/201; A47L 11/26; A47L 11/28;
(Continued)

(56) References Cited

U.S. PATENT DOCUMENTS 3,729,041 A    4/1973 Kubota
4,319,379 A    3/1982 Carrigan et al.
(Continued)

FOREIGN PATENT DOCUMENTS

DE    8501727    6/1985
EP    1602313    12/2005
(Continued)

OTHER PUBLICATIONS

Partial European Search Report issued in European Application No. 14861203.9 dated Sep. 28, 2016, 7 pages.
(Continued)

*Primary Examiner* — Mark Spisich
(74) *Attorney, Agent, or Firm* — Fish & Richardson P.C.

(57) ABSTRACT

A pad particularly adapted for surface cleaning. The pad includes an absorbent core having the ability to absorb and retain liquid material, and a liner layer in contact with and covering at least one side of the absorbent core. The liner layer has the ability to retain and wick liquid material through the liner layer. Cleaning apparatus containing such pads and methods of using such pads are also described.

20 Claims, 21 Drawing Sheets

Related U.S. Application Data continuation-in-part of application No. 14/077,296, filed on Nov. 12, 2013, now Pat. No. 9,427,127.

(60) Provisional application No. 61/902,838, filed on Nov. 12, 2013, provisional application No. 62/059,637, filed on Oct. 3, 2014.

(51) Int. Cl.

| | | |
|---|---|---|
| *A47L 11/284* | (2006.01) | |
| *A47L 11/12* | (2006.01) | |
| *A47L 13/20* | (2006.01) | |
| *A47L 13/16* | (2006.01) | |
| *A61F 13/36* | (2006.01) | |
| *B32B 5/02* | (2006.01) | |
| *B32B 7/12* | (2006.01) | |
| *B32B 25/14* | (2006.01) | |
| *B32B 29/00* | (2006.01) | |
| *B32B 3/04* | (2006.01) | |
| *B32B 5/26* | (2006.01) | |

(52) U.S. Cl.
CPC ........ *A47L 11/408* (2013.01); *A47L 11/4036* (2013.01); *A47L 11/4066* (2013.01); *A47L 11/4069* (2013.01); *A47L 11/4072* (2013.01); *A47L 11/4088* (2013.01); *A47L 13/16* (2013.01); *A47L 13/20* (2013.01); *A61F 13/36* (2013.01); *B32B 3/04* (2013.01); *B32B 5/022* (2013.01); *B32B 7/12* (2013.01); *B32B 25/14* (2013.01); *B32B 29/002* (2013.01); *A47L 2201/00* (2013.01); *A47L 2201/04* (2013.01); *A47L 2201/06* (2013.01); *B32B 5/26* (2013.01); *B32B 2255/12* (2013.01); *B32B 2262/04* (2013.01); *B32B 2262/067* (2013.01); *B32B 2262/14* (2013.01); *B32B 2307/718* (2013.01); *B32B 2307/7145* (2013.01); *B32B 2307/726* (2013.01); *B32B 2307/73* (2013.01); *B32B 2432/00* (2013.01)

(58) Field of Classification Search
CPC ........ A47L 11/29; A47L 11/30; A47L 11/40; A47L 11/4011; A47L 11/4036; A47L 11/4063; A47L 11/4066; A47L 11/408; A47L 11/4088
USPC ............... 15/319, 320, 340.1, 403, 50.1, 98
See application file for complete search history.

(56) References Cited

U.S. PATENT DOCUMENTS

| | | | |
|---|---|---|---|
| 4,967,862 | A | 11/1990 | Pong et al. |
| 5,440,216 | A | 8/1995 | Kim |
| 5,609,255 | A | 3/1997 | Nichols |
| 5,630,243 | A | 5/1997 | Federico et al. |
| 5,720,077 | A | 2/1998 | Nakamura et al. |
| 5,787,545 | A | 8/1998 | Colens |
| 5,815,880 | A | 10/1998 | Nakanishi |
| 5,841,259 | A | 11/1998 | Kim et al. |
| 5,894,621 | A | 4/1999 | Kubo |
| 5,940,927 | A | 8/1999 | Haegermarck et al. |
| 5,959,423 | A | 9/1999 | Nakanishi et al. |
| 5,991,951 | A | 11/1999 | Kubo et al. |
| 5,998,953 | A | 12/1999 | Nakamura et al. |
| 6,012,618 | A | 1/2000 | Matsuo |
| 6,076,025 | A | 6/2000 | Ueno et al. |
| 6,101,661 | A | 8/2000 | Policicchio |
| 6,119,057 | A | 9/2000 | Kawagoe |
| 6,142,252 | A | 11/2000 | Kinto et al. |
| 6,327,741 | B1 | 12/2001 | Reed |
| 6,338,013 | B1 | 1/2002 | Ruffner |
| 6,389,329 | B1 | 5/2002 | Colens |
| 6,459,955 | B1 | 10/2002 | Bartsch et al. |
| 6,481,515 | B1 | 11/2002 | Kirkpatrick et al. |
| 6,491,998 | B1 | 12/2002 | Heitz |
| 6,532,404 | B2 | 3/2003 | Colens |
| 6,580,246 | B2 | 6/2003 | Jacobs |
| 6,594,844 | B2 | 7/2003 | Jones |
| 6,600,981 | B2 | 7/2003 | Ruffner |
| 6,690,134 | B1 | 2/2004 | Jones et al. |
| 6,741,054 | B2 | 5/2004 | Koselka et al. |
| 6,771,217 | B1 | 8/2004 | Liu et al. |
| 6,779,217 | B2 | 8/2004 | Fisher |
| 6,781,338 | B2 | 8/2004 | Jones et al. |
| 6,809,490 | B2 | 10/2004 | Jones et al. |
| 6,868,307 | B2 | 3/2005 | Song et al. |
| 6,883,201 | B2 | 4/2005 | Jones et al. |
| 6,901,624 | B2 | 6/2005 | Mori et al. |
| 6,938,298 | B2 | 9/2005 | Aasen |
| 6,965,209 | B2 | 11/2005 | Jones et al. |
| 6,996,871 | B1 | 2/2006 | Policicchio |
| 7,013,527 | B2 | 3/2006 | Thomas et al. |
| 7,013,528 | B2 | 3/2006 | Parker et al. |
| 7,015,831 | B2 | 3/2006 | Karlsson et al. |
| 7,113,847 | B2 | 9/2006 | Chmura et al. |
| 7,135,992 | B2 | 11/2006 | Karlsson et al. |
| 7,137,169 | B2 | 11/2006 | Murphy et al. |
| 7,145,478 | B2 | 12/2006 | Goncalves et al. |
| 7,155,308 | B2 | 12/2006 | Jones |
| 7,162,338 | B2 | 1/2007 | Goncalves et al. |
| 7,173,391 | B2 | 2/2007 | Jones et al. |
| 7,177,737 | B2 | 2/2007 | Karlsson et al. |
| 7,196,487 | B2 | 3/2007 | Jones et al. |
| 7,248,951 | B2 | 7/2007 | Hulden |
| 7,272,467 | B2 | 9/2007 | Goncalves et al. |
| 7,320,149 | B1 | 1/2008 | Huffman et al. |
| 7,346,428 | B1 | 3/2008 | Huffman et al. |
| 7,388,343 | B2 | 6/2008 | Jones et al. |
| 7,389,156 | B2 | 6/2008 | Ziegler et al. |
| 7,448,113 | B2 | 11/2008 | Jones et al. |
| 7,480,958 | B2 | 1/2009 | Song et al. |
| 7,539,557 | B2 | 5/2009 | Yamauchi |
| 7,571,511 | B2 | 8/2009 | Jones et al. |
| 7,620,476 | B2 | 11/2009 | Ziegler et al. |
| 7,636,982 | B2 | 12/2009 | Jones et al. |
| 7,761,954 | B2 | 7/2010 | Ziegler et al. |
| 7,832,048 | B2 | 11/2010 | Harwig et al. |
| 7,891,898 | B2 | 2/2011 | Hoadley et al. |
| 8,387,193 | B2 | 3/2013 | Ziegler et al. |
| 8,670,866 | B2 | 3/2014 | Ziegler et al. |
| 8,692,695 | B2 | 4/2014 | Fallon et al. |
| 8,739,355 | B2 | 6/2014 | Ziegler et al. |
| 8,774,966 | B2 | 7/2014 | Ziegler et al. |
| 8,782,848 | B2 | 7/2014 | Ziegler et al. |
| 8,855,813 | B2 | 10/2014 | Ziegler et al. |
| 8,892,251 | B1 | 11/2014 | Dooley et al. |
| 8,931,971 | B2 | 1/2015 | Schwarz et al. |
| 8,961,695 | B2 | 2/2015 | Romanov et al. |
| 8,966,707 | B2 | 3/2015 | Ziegler et al. |
| 2002/0002751 | A1 | 1/2002 | Fisher |
| 2002/0011813 | A1 | 1/2002 | Koselka et al. |
| 2002/0016649 | A1 | 2/2002 | Jones |
| 2002/0083964 | A1 | 7/2002 | McKay |
| 2002/0120364 | A1 | 8/2002 | Colens |
| 2002/0175648 | A1 | 11/2002 | Erko et al. |
| 2003/0025472 | A1 | 2/2003 | Jones et al. |
| 2003/0028985 | A1 | 2/2003 | Prodoehl et al. |
| 2003/0229421 | A1 | 12/2003 | Chmura et al. |
| 2004/0020000 | A1 | 2/2004 | Jones |
| 2004/0031113 | A1 | 2/2004 | Wosewick et al. |
| 2004/0049877 | A1 | 3/2004 | Jones et al. |
| 2004/0128786 | A1 | 7/2004 | Policicchio et al. |
| 2004/0143930 | A1 | 7/2004 | Haegermarck |
| 2004/0187457 | A1 | 9/2004 | Colens |
| 2004/0207355 | A1 | 10/2004 | Jones et al. |
| 2004/0244138 | A1 | 12/2004 | Taylor et al. |
| 2005/0028316 | A1 | 2/2005 | Thomas et al. |
| 2005/0053912 | A1 | 3/2005 | Roth et al. |
| 2005/0067994 | A1 | 3/2005 | Jones et al. |
| 2005/0155631 | A1 | 7/2005 | Kilkenny et al. |

(56) References Cited

U.S. PATENT DOCUMENTS

| | | |
|---|---|---|
| 2005/0204717 A1 | 9/2005 | Colens |
| 2005/0209736 A1 | 9/2005 | Kawagoe |
| 2005/0217061 A1 | 10/2005 | Reindle |
| 2005/0229340 A1 | 10/2005 | Sawalski et al. |
| 2005/0229344 A1 | 10/2005 | Mittelstaedt et al. |
| 2005/0278888 A1 | 12/2005 | Reindle et al. |
| 2006/0009879 A1 | 1/2006 | Lynch et al. |
| 2006/0085095 A1 | 4/2006 | Reindle et al. |
| 2006/0123587 A1 | 6/2006 | Parr et al. |
| 2006/0184293 A1* | 8/2006 | Konandreas ........ A47L 11/4072 701/23 |
| 2006/0185690 A1 | 8/2006 | Song et al. |
| 2006/0190134 A1 | 8/2006 | Ziegler et al. |
| 2006/0200281 A1 | 9/2006 | Ziegler et al. |
| 2006/0207053 A1 | 9/2006 | Beynon |
| 2006/0288519 A1 | 12/2006 | Jaworski et al. |
| 2006/0293794 A1 | 12/2006 | Harwig et al. |
| 2006/0293809 A1 | 12/2006 | Harwig et al. |
| 2007/0016328 A1 | 1/2007 | Ziegler et al. |
| 2007/0061040 A1 | 3/2007 | Augenbraun et al. |
| 2007/0094836 A1 | 5/2007 | Sepke et al. |
| 2007/0226943 A1 | 10/2007 | Lenkiewicz et al. |
| 2007/0234492 A1 | 10/2007 | Svendsen et al. |
| 2007/0266508 A1 | 11/2007 | Jones et al. |
| 2008/0039974 A1 | 2/2008 | Sandin et al. |
| 2008/0104783 A1 | 5/2008 | Crawford et al. |
| 2008/0109126 A1 | 5/2008 | Sandin et al. |
| 2008/0127446 A1 | 6/2008 | Ziegler et al. |
| 2008/0140255 A1 | 6/2008 | Ziegler et al. |
| 2008/0155768 A1 | 7/2008 | Ziegler et al. |
| 2008/0188984 A1 | 8/2008 | Harwig et al. |
| 2008/0244846 A1 | 10/2008 | Bayon et al. |
| 2008/0307590 A1 | 12/2008 | Jones et al. |
| 2009/0133720 A1 | 5/2009 | Van Den Bogert |
| 2009/0281661 A1 | 11/2009 | Dooley et al. |
| 2009/0306822 A1 | 12/2009 | Augenbraun et al. |
| 2010/0049365 A1 | 2/2010 | Jones et al. |
| 2010/0223748 A1 | 9/2010 | Lowe et al. |
| 2010/0257690 A1 | 10/2010 | Jones et al. |
| 2010/0257691 A1 | 10/2010 | Jones et al. |
| 2010/0263158 A1 | 10/2010 | Jones et al. |
| 2014/0259511 A1 | 9/2014 | Ziegler et al. |
| 2014/0289992 A1 | 10/2014 | Ziegler et al. |

FOREIGN PATENT DOCUMENTS

| | | |
|---|---|---|
| EP | 1625949 | 2/2006 |
| EP | 1695652 | 8/2008 |
| EP | 1909630 | 7/2014 |
| JP | S63315169 | 12/1988 |
| JP | H09-135800 | 5/1997 |
| JP | 2000507481 | 6/2000 |
| JP | 3074647 | 12/2000 |
| JP | 2001521432 | 11/2001 |
| JP | 2003534086 | 11/2003 |
| JP | 2005138749 | 6/2005 |
| JP | 2005533567 | 11/2005 |
| JP | 2005342259 | 12/2005 |
| JP | 2006512951 | 4/2006 |
| JP | 2010201112 | 9/2010 |
| JP | 2010500087 | 10/2010 |
| JP | 2012176279 | 9/2012 |
| KR | 10-0236742 | 3/2000 |
| KR | 10-2012-0042391 | 5/2012 |
| WO | 9842246 | 10/1998 |
| WO | 20010091623 | 12/2001 |
| WO | 20010091624 | 12/2001 |
| WO | 2006121805 | 11/2006 |

OTHER PUBLICATIONS

Invitation to Pay Additional Fees issued in International Application No. PCT/US2014/065004, dated Jan. 23, 2015, 2 pages.

International Search Report and Written Opinion issued in International Application No. PCT/US2014/065004, dated Apr. 6, 2015, 11 pages.

Anderson, "IMU Odometry," Jul. 27, 2006, [retrieved on Aug. 4, 2015], available at URL: http://www_geology_smu_edu/dpa-www/robo/Encoder/imu_odo/, 19 pages.

Anderson and Hamilton, "The Journey Robot," Aug. 1, 2005, [retrieved on Aug. 4, 2015], Southern Methodist University, available at URL: http:/fwww_geology_smu.edu/-dpa-www/robo/jbot/, 10 pages.

Schur et al., "Robotics and Artificial Lifeforms: Stasis Logic," Feb. 5, 2007, [retrieved on Aug. 4, 2015], available at URL: http://www_schursastrophotography_com/robotics/stasislogic_html, 4 pages.

International Search Report and Written Opinion issued in International Application No. PCT/US2014/062096, dated Feb. 4, 2015, 17 pages.

European Search Report in European Application No. 18202105.5, dated Jan. 30, 2019, 6 pages.

* cited by examiner

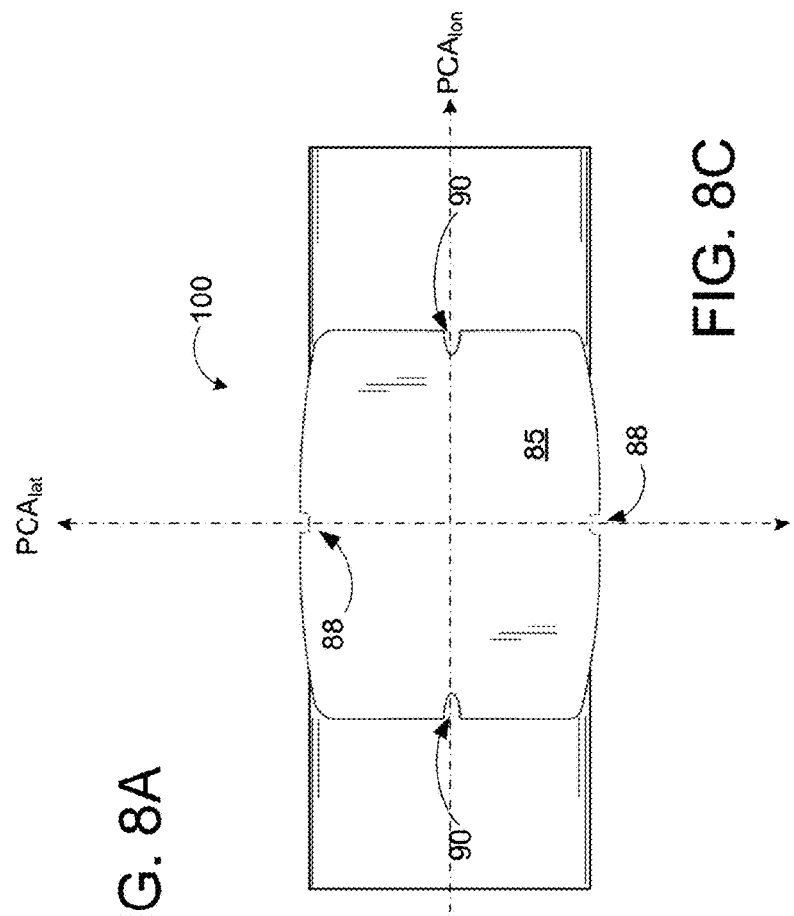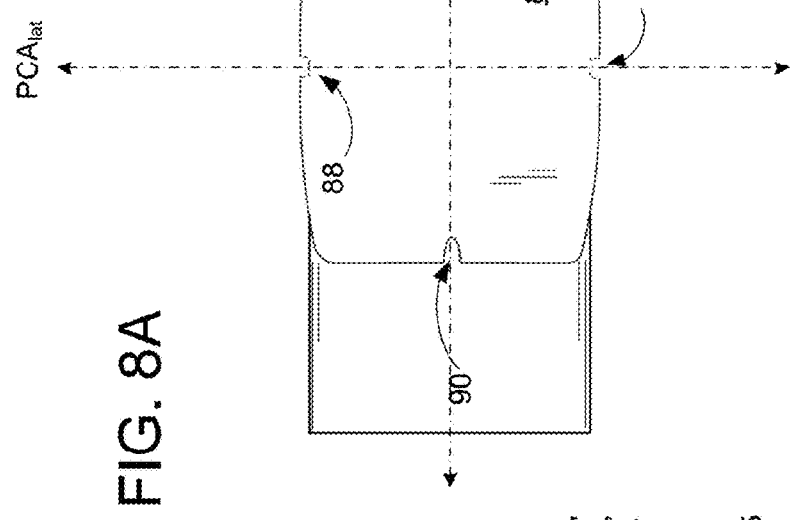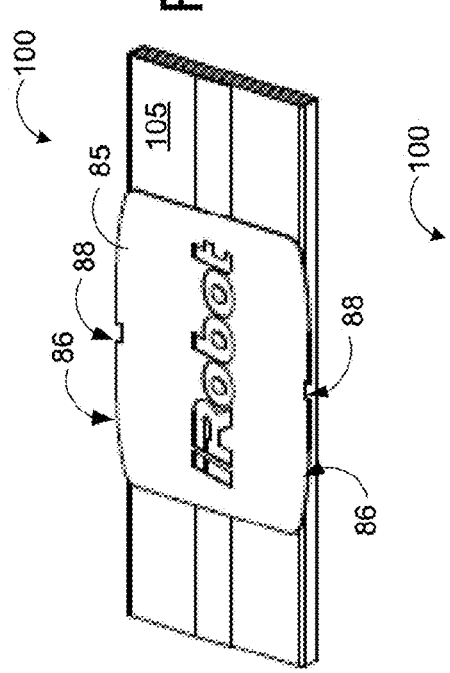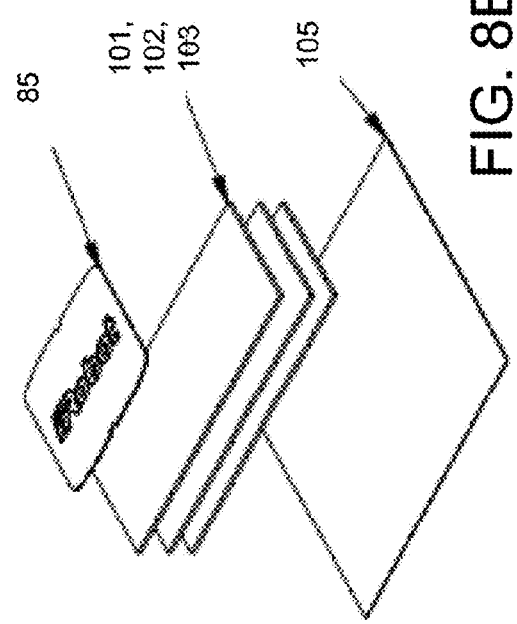

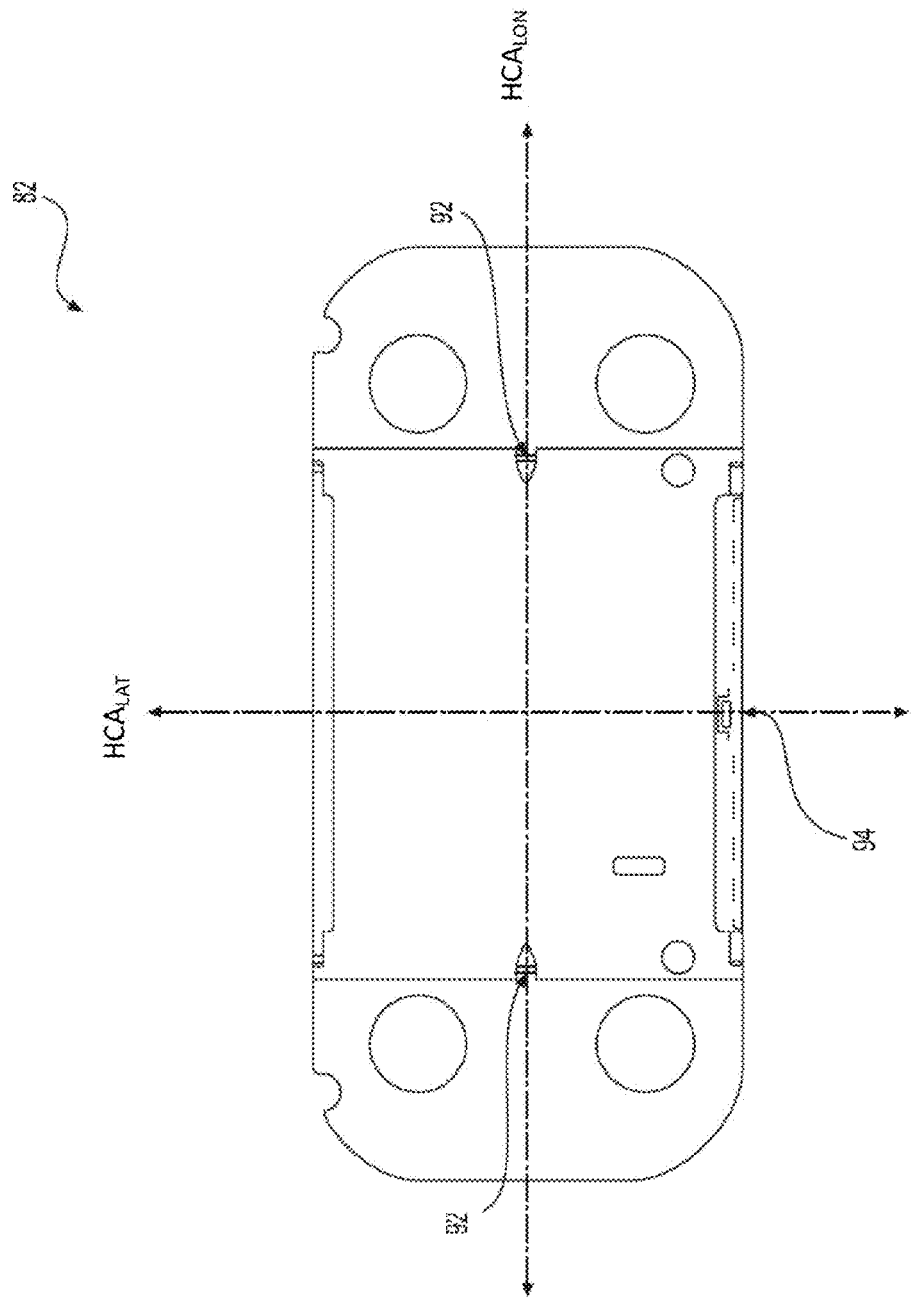

FLOOR CLEANING ROBOT

CROSS-REFERENCE TO RELATED APPLICATIONS

This application is a Continuation of U.S. patent application Ser. No. 14/538,349, filed Nov. 11, 2014, now U.S. Pat. No. 9,615,712, which is a Continuation-In-Part of U.S. application Ser. No. 14/077,296 entitled "Autonomous Surface Cleaning Robot" filed Nov. 12, 2013 now U.S. Pat. No. 9,427,127, which claims the benefit of U.S. Provisional Patent Application Ser. No. 61/902,838 entitled "Cleaning Pad" filed Nov. 12, 2013, and U.S. Provisional Patent Application Ser. No. 62/059,637 entitled, "Surface Cleaning Pad" filed Oct. 3, 2014. Each of the aforementioned applications is assigned to an entity common hereto. Further, the entirety of each one of the aforementioned patent applications is incorporated herein by reference for all purposes.

TECHNICAL FIELD

This disclosure relates to floor cleaning using a cleaning pad.

BACKGROUND

Tiled floors and countertops routinely need cleaning, some of which entails scrubbing to remove dried in soils. Various cleaning implements can be used for cleaning hard surfaces. Most implements include a cleaning pad that may be removably attached to the implement. The cleaning pads may be disposable or reusable. In some examples, the cleaning pads are designed to fit a specific implement or may be designed for more than one implement.

Traditionally, wet mops are used to remove dirt and other dirty smears (e.g., dirt, oil, food, sauces, coffee, coffee grounds) from the surface of a floor. A person usually dips the mop in a bucket of water and soap or a specialized floor cleaning solution and rubs the floor with the mop. In some examples, the person may have to perform back and forth scrubbing movements to clean a specific dirt area. The person then dips the mop in the same bucket of water to clean the mop and continues to scrub the floor. Additionally, the person may need to kneel on the floor to clean the floor, which could be cumbersome and exhausting, especially when the floor covers a large area.

Floor mops are used to scrub floors without the need for a person go on their knees. A pad attached to the mop or an autonomous robot can scrub and remove solids from surfaces and prevents a user from bending over to clean the surface, which prevents a injuries to the user.

SUMMARY

A surface cleaning pad is described including an absorbent core containing fiber material which absorbs and retains liquid material, a liner layer (also herein throughout called a "wrap layer") in contact with and covering at least one side of the absorbent core, containing fiber material which retains and wicks liquid material through the liner layer. In embodiments, the cleaning pad is disposable or washable and reusable.

Additional embodiments include the following elements or characteristics taken in combination or sub-combination to provide the advantages of absorbing and retaining fluid and suspended debris for a compact mobile robot weighing less than 2.25 kg. The following elements or characteristics taken in combination or sub-combination create a pad that wicks moisture and debris into the absorbent core without expanding and raising the front edge of the lightweight robot, which would impede the movement pattern and cleaning efficacy of the robot because maximum downward force, such as 1 pound of force, would no longer be applied to the pad: the pad described above where the pad absorbs about 20 milliliters of liquid material in about 10 seconds with about 0.9 pounds of pressure on the pad; the pad described above where the absorbent core retains up to about 90% by volume of the liquid material absorbed; the pad described above where the liquid material is substantially evenly distributed throughout the absorbent core; the pad described above where the core material absorbs up to about 7 to about 10 times its weight; the pad described above where the liner layer retains up to about 10% of the liquid material absorbed; the pad described above where the absorbent core comprises cellulose fibers; the pad described above where the absorbent core comprises a mixture of cellulosic and polymer fibers; the pad described above where the absorbent core comprises non-woven cellulose pulp; the pad described above where the cellulose pulp is polymer bonded; the pad described above where the polymer comprises polyethylene and/or polypropylene; the pad described above where the absorbent core additionally contains a surface layer comprising acrylic latex, for example, to eliminate linting; the pad described above where the pad does not substantially compress or expand when absorbing or retaining liquid, for example, when wet; the pad described above where the pad includes a backing layer attached to the pad and particularly adapted to attach the pad to a cleaning apparatus; the pad described above where the backing layer comprises cardboard; the pad described above where the cardboard backing layer is between 0.1 and 0.05 inch thick (0.254 cm to 0.127 cm thick); the pad described above where the cardboard backing layer is 0.028 inch thick (0.07 cm thick); the pad described above where the pad is coated with a polymer; the pad described above where the polymer coating is about 0.010 to about 0.040 inch thick (0.0254 cm to 0.1016 cm thick); the pad described above where the polymer is any polymer or wax material that can seal against liquid penetration, such as water, for example (such as polyvinyl alcohol or polyamine, for example); the pad described above where the cardboard is attached to the pad with an adhesive; the pad described above where the absorbent core comprises first, second, and third airlaid layers, each airlaid layer having a top surface and a bottom surface, the bottom surface of the first airlaid layer disposed on the top surface of the second airlaid layer, the bottom surface of the second airlaid layer disposed on the top surface of the third airlaid layer; the pad described above where the liner layer is wrapped around and covers at least two sides of the absorbent core; the pad described above where the liner layer comprises a spunlace layer; the pad described above where the liner layer comprises a hydroentangled spunbond or spunlace layer having reduced thickness indentations therein on a floor facing surface and having a basis weight of 35-40 gsm (grams per square meter). When a pad 100 is damp, not enough fluid is present to lubricate the interface between the bottom surface of the pad and the floor surface. A fully wetted pad will ride on a layer of fluid while the pad is moving over a floor surface, but as the damp pad slowly absorbs fluid, the not fully wet, not fully lubricated, wrap layer will drag on the floor surface. In implementations, the spunbond or spunlace wrap layer is manufactured with hydrophilic fibers that minimize the surface area of the pad exposed to air between the pad and the floor surface. A wet pad would stick to the hydrophilic floor surface if the indentations or needle punches were not part of the wrap layer. Applying a surface texture to the spunbond or spunlace of the wrap layer, such as a herringbone indentation patter or a square grid indentation pattern, breaks the surface tension that would otherwise case a wet pad to stick to a wet floor surface.

In implementations of the pad, the liner layer includes meltblown abrasive fibers adhered to the side of the liner layer not in contact with the absorbent core; the pad described above where the meltblown fibers have a diameter of between about 0.1 µm and about 20 µm; the pad described above where the meltblown abrasive fibers cover between about 44 percent and about 75 percent of the surface of the liner layer; In implementations of the pad, the meltblown abrasive fibers cover between about 50% and about 60% of the surface of the liner layer. The meltblown layer provides the pad with the advantages of breaking surface tension that might otherwise cause the wet wrap layer to stick to a wet floor. By adding texture and topography to a floor facing surface of the pad, the meltblown layer prevents the pad from sticking or encountering high drag forces. The meltblown layer also provides the pad with surface texture for roughing up dirt and debris stuck or dried to a floor surface and loosening dirt and debris for absorption by the airlaid inner core of the pad. In implementations of the pad the meltblown abrasive fibers and the liner layer have a collective thickness of between about 0.5 mm (millimeter) and about 0.7 mm. In other words, the maximum overlapped thickness from the outer layer of the applied meltblown to the surface of the wrap layer is 0.7 mm. In implementations of the pad, the wrap layer has a thickness of between about 0.5 mm and about 0.7 mm. In implementations, the wrap layer has a Worldwide Strategic Partners (WSP) 10.1(05) nonwoven materials water absorption test specification value of about 600%; the pad described above where the pad increases in thickness by less than 30% after liquid material absorption. In implementations, the pad additionally contains one or more of a scent agent, cleaning agent, surfactant, foaming agent, glossing agent, chemical preservative, debris retention agent (such as DRAKESOL) and/or anti-bacterial agent. In implementations, the pad has a thickness of between about 6.5 mm and about 8.5 mm. In implementations, the pad has a width of between about 68 millimeters and about 80 millimeters and a length of between about 165 millimeters and about 212 millimeters. In implementations, the liner layer has a width of between about 163 millimeters and about 169 millimeters and a length between about 205 millimeters and about 301 millimeters. In implementations, the absorbent core comprises a first airlaid layer adhered to a second airlaid layer and the second airlaid layer is adhered to a third airlaid layer.

Fluid wicks between the three layers and is retained uniformly vertically throughout the stack of airlaid layers without leaking back onto a floor surface beneath the cleaning pad while downward force is applied to the pad. In implementations, the pad retains 90 percent of fluid applied to a floor surface and under 1 pound of force, the pad does not leak absorbed fluid back onto the floor surface. The surface tension the top and bottom surfaces of each airlaid layer helps retain wicked fluid within each layer such that as the top layer fully saturates, no fluid will leak down to the middle airlaid layer through the bottom surface 11b of the top airlaid layer, and as the middle airlaid layer fully saturates, no fluid will leak down to the bottom layer through the bottom surface of the middle (or second) layer.

In implementations, the pad soaks up 8-10 times its weight in fluid into a relatively rigid matrix of airlaid layers that does not deform in any dimension when fully wet, and fluid absorption is achieved through capillary wicking, not by compress-release drawing because robot to which the pad is attached exerts very light, low variability cycle weight, not a cycle of heavy human push down and draw back. Each of airlaid layer slows down penetration of wicked fluid to the next adjacent airlaid layer such that early cycles of fluid application do not lead to the pay quickly sopping up all the fluid that is applied to the floor surface. The vertical stack of airlaid layers provides a resistance to puddling at the bottom of the airlaid core comprising the three airlaid layers. Each of the of airlaid layers has its own puddle resisting bottom surface for preventing puddling of absorbed fluid all the way down at the bottom of the bottom surface of the bottom (or third) layer.

In implementations, the airlaid layers are of non-uniform hardness or density in the vertically direction such the outer top and bottom surfaces are harder than the interior of each layer. In embodiments, as a characteristic of the manufacturing process, the airlaid layers are of non-uniform surface density such that the outer top and bottom surfaces are smoother and less absorptive than the interior of each layer. By varying the surface density at the outer surfaces of each of the airlaid layer, the airlaid layers remain absorptive, wicking fluid into each airlaid layer without leaking back through the bottom surfaces. By incorporating three such airlaid layers into the absorptive core of the pad, the pad therefore has superior fluid retention properties over a pad having a single core of thickness equivalent to the three layer stacked core. The three airlaid layers provide at least triple the amount of surface tension for In implementations of the pad, the three airlaid layers are adhered to each other by means of an adhesive material. In some implementations, the adhesive material is applied in at least two evenly spaced strips along the length of at least one side of an airlaid layer and covers not more than 10% of the surface area of the at least one side. In implementations, of the pad the adhesive material is sprayed on the length of at least one side of an airlaid layer and covers not more than 10% of the surface area of the at least one side. In implementations of the pad, at least one airlaid layer comprises a cellulose based textile material. In some implementations, at least one airlaid layer, and preferably all three airlaid layers, comprises wood pulp. In some implementations, one or more of the airlaid layers comprises biocomponent polymers, cellulose, and latex and the polymer is present in an amount up to about 15% by weight.

A method for constructing a cleaning pad is also described, including disposing a first airlaid layer on a second airlaid layer; disposing the second airlaid layer on a third airlaid layer; and wrapping a wrap layer around the first, second, and third airlaid layers, the wrap layer comprising: a fiber composition; and a meltblown abrasive adhered to the fiber composition on an outer surface positioned to interface with a floor surface beneath the cleaning pad, the fiber composition being a spunlace or spunbond material.

Additional embodiments of the method for constructing a cleaning pad include the following elements or characteristics taken in combination or sub-combination to provide the advantages of scrubbing debris from a floor surface and absorbing and retaining fluid and suspended debris when the pad is attached to a compact mobile robot weighing less than 2.25 kg without impeding the back and forth birdsfoot or vining scrubbing pattern and cleaning efficacy of the robot.

The following elements or characteristics taken in combination or sub-combination create a pad that wicks moisture and debris into the absorbent core without expanding and raising the front edge of the lightweight robot, which would prevent the robot from applying maximum downward force to the pad: the method further comprising adhering and randomly arranging meltblown abrasive fibers on the wrap layer; the method described above where the meltblown abrasive fibers having a diameter of between about 8 µm and about 20 µm; the method described above further comprising arranging the meltblown abrasive and the wrap layer to have a collective thickness of between about 0.5 mm and about 0.7 mm; the method described above further comprising arranging the meltblown abrasive on the wrap layer to provide a covered surface ratio between the meltblown abrasive and the wrap layer of between about 44% and 57%; the pad described above where the meltblown abrasive fibers cover between about 50% and about 60% of the surface of the liner layer; the method described above further comprising adhering the first airlaid layer to the second airlaid layer and adhering the second airlaid layer to the third airlaid layer; the method described above where the airlaid layer is a cellulose based textile material; the method described above where the first, second, and third airlaid layers, the spunlace layer, and the meltblown abrasive are configured to increase in thickness by less than 30% after fluid absorption; the method described above further comprising configuring the airlaid layers and wrap layer to have a combined width of between about 80 millimeters and about 68 millimeters and a combined length of between about 200 millimeters and about 212 millimeters; the method described above further comprising configuring the airlaid layers and the wrap layer to have a combined thickness of between about 6.5 millimeters and about 8.5 millimeters; the method described above further comprising configuring the airlaid layers have a combined airlaid width of between about 69 millimeters and about 75 millimeters and a combined airlaid length between about 165 millimeters and about 171 millimeters.

A surface cleaning apparatus is also described having attached thereto the cleaning pad described above. Additional embodiments include where the surface cleaning apparatus is a mop or autonomous mobile robot; the surface cleaning apparatus described above where the pad is releaseably attached to the surface cleaning apparatus through a backing layer attached to the pad; the surface cleaning apparatus described above where the backing layer comprises cardboard; and the surface cleaning apparatus described above where the surface cleaning apparatus additionally contains a release mechanism to eject the releaseably attached pad.

A method of cleaning a surface with the pad described above is also described, including applying a surface cleaning liquid to the surface to be cleaned and passing the surface cleaning pad over the surface. The pad absorbs about 20 milliliters of liquid material in about 10 seconds with about 400 gram-force of pressure on the pad. In some implementations, the absorbent core retains up to about 90% by volume of the liquid material absorbed. In some implementations, liquid material absorbed is substantially evenly distributed throughout the core. In some implementations, the core material absorbs up to about 7 to about 10 times its weight. In some implementations, the liner layer retains up to about 10% of the liquid material absorbed.

A mobile robot is also described. In implementations, the robot includes a robot body defining a forward drive direction, a drive supporting the robot body to maneuver the robot across a floor surface, and a cleaning assembly disposed on the robot body. The cleaning assembly includes a pad holder configured to receive a cleaning pad having a center and lateral edges, and the pad holder comprises a release mechanism configured to eject the pad upon actuation of a release mechanism. The robot further includes a fluid applicator configured to apply fluid to the floor surface, wherein, and a controller circuit in communication with the drive and the cleaning assembly, the controller circuit controlling the drive and fluid applicator while executing a cleaning routine. The cleaning routine includes applying fluid to a floor surface area substantially equal to a footprint area of the robot, and returning the robot to the floor surface area in a movement pattern that moves the center and lateral edges of the cleaning pad separately through the floor surface area to moisten the entire surface area of the cleaning pad with the applied fluid.

Additional implementations include the robot described above where the cleaning routine further comprises applying fluid to the floor surface at an initial volumetric flow rate to moisten the cleaning pad, the initial volumetric flow rate being relatively higher than a subsequent volumetric flow rate when the cleaning pad is moistened. In one implementation, the first volumetric flow rate is set by spraying about 1 mL of fluid every 1.5 feet initially for a period of time such as 1-3 minutes, and the second volumetric flow rate is set by spraying every 3 feet, wherein each spray of fluid is less than 1 mL of volume. The fluid applicator applies fluid to a floor surface area in front of the cleaning pad and in the forward drive direction of the mobile robot, and the fluid is applied to a floor surface area previously occupied by the cleaning pad. In implementations, the previously occupied floor surface area is stored on a map accessible to the controller circuit. In implementations, fluid is applied to a floor surface area the robot has backed away from by a distance of at least one robot footprint length immediately prior to applying fluid so that the fluid is only applied to traversable floor and not to a wall, piece of furniture, carpet or other non-floor area that triggers a bump sensor (collision) switch or proximity sensor on the robot. In implementations, executing the cleaning routine further comprises moving the cleaning pad in a birdsfoot motion forward and backward along a center trajectory, forward and backward along a trajectory to a left side of and heading away from a starting point along the center trajectory, and forward and backward along a trajectory to a right side of and heading away from a starting point along the center trajectory. The robot drive comprises right and left drive wheels disposed on corresponding right and left portions of the robot body, and a center of gravity of the robot is positioned forward of the drive wheels, causing a majority of an overall weight of the robot to be positioned over the pad holder. Because the pad does not expand during fluid absorption, the weight of the robot remains positioned over the pad holder throughout the cleaning routine. The overall weight of the robot is distributed between the pad holder and the drive wheels at a ratio of 3 to 1, and the overall weight of the robot without retaining any fluid is between about 1 kg and about 1.5kg and with retaining fluid is between about 1.5 kg to 4.5 kg. In implementations, the robot body and the pad holder both define substantially rectangular foot prints. Additionally, in implementations, the robot further includes a vibration motor disposed on a top portion of the pad holder. In some implementations, the robot further includes a toggle button for actuating the pad holder release mechanism and ejecting the pad. A backing layer on the pad engages with the pad holder, and the pad holder comprises raised protrusions positioned for aligning to and engaging with one or more shaped slots cut out of the backing layer along a peripheral edge of the backing layer. In some implementations, the pad holder comprises raised protrusions positioned for aligning to and engaging with one or more shaped slots cut out of the backing layer at a location other than along a peripheral edge.

A mobile floor cleaning robot is also described including a robot body defining a forward drive direction, a drive supporting the robot body to maneuver the robot across a surface, the drive comprising right and left drive wheels disposed on corresponding right and left portions of the robot body. The robot includes a cleaning assembly disposed on the robot body, the cleaning assembly having a pad holder disposed forward of the drive wheels and having a top portion and a bottom portion, the bottom portion having a bottom surface arranged within between about 0.5 cm and about 1.5 cm of the surface and configured to receive a cleaning pad. The bottom surface of the pad holder includes at least 40 percent of a surface area of a footprint of the robot, and the bottom surface having one or more raised protrusions extending therefrom for engaging with mating slots on a pad assembly. In implementations, the robot includes an orbital oscillator having less than 1 cm of orbital range disposed on the top portion of the pad holder. The pad holder is configured to permit more than 80 percent of the orbital range of the orbital oscillator to be transmitted from the top of the received cleaning pad to the bottom surface of the received cleaning pad. The one or more protrusions assist with aligning the pad to the pad holder and retaining the pad securely in place during oscillation of the orbital oscillation while the robot moves in a back and forth scrubbing cleaning pattern. In implementations, the pad holder includes a release mechanism configured to eject the pad from the bottom surface of the pad holder upon actuation of the release mechanism such that a user need not touch a used, dirty pad to dispose of it. Actuating the release mechanism while holding the robot above a trash container ejects the pad from the pad holder into the trash container therebeneath.

In some implementations, the orbital range of the orbital oscillator is less than 0.5 cm during at least part of a cleaning run. Additionally, the robot drives forward and backward while oscillating the cleaning pad. In implementations, the robot drives in a birdsfoot motion to move the cleaning pad forward and backward along a center trajectory, forward and backward along a trajectory to a left side of and heading away from a starting point along the center trajectory, and forward and backward along a trajectory to a right side of and heading away from a starting point along the center trajectory. The cleaning pad has a top surface attached to the bottom surface of the pad holder and the top of the pad is substantially immobile relative to the oscillating pad holder. In implementations, the robot cleaning assembly further includes a reservoir to hold a volume of fluid and a fluid applicator in fluid communication with the reservoir. The fluid applicator is configured to apply the fluid along the forward drive direction forward of the pad holder. The cleaning pad is configured to absorb about 90 percent of the fluid volume held in the reservoir without leaking onto the floor surface beneath the pad while receiving 1 pound of downward force. The pad further includes a backing layer on the cleaning pad for engaging with the pad holder and one or more raised protrusions on the bottom of the pad holder are positioned for aligning to and engaging with shaped slots cut out of the backing layer. The one or more protrusions assist with aligning the pad to the pad holder and retaining the pad securely in place during oscillation of the orbital oscillation while the robot moves in a back and forth scrubbing cleaning pattern. In implementations, the pad holder includes a release mechanism configured to eject the pad from the bottom surface of the pad holder upon actuation of the release mechanism such that a user need not touch a used, dirty pad to dispose of it. Actuating the release mechanism while holding the robot above a trash container ejects the pad from the pad holder into the trash container therebeneath.

A method of operating a mobile floor cleaning robot is also described including driving in a forward drive direction defined by the robot a first distance to a first location while moving a cleaning pad carried by the robot along a floor surface supporting the robot, the cleaning pad having a center and lateral edges; driving in a reverse drive direction, opposite the forward drive direction, a second distance to a second location while moving the cleaning pad along the floor surface; from the second location, applying fluid to an area substantially equal to a footprint area of the robot on the floor surface in the forward drive direction forward of the cleaning pad but rearward of the first location; and returning the robot to the area in a movement pattern that moves the center and lateral edges of the cleaning pad separately through the area to moisten the cleaning pad with the applied fluid.

Additional embodiments include: the method described above further comprising driving in a left drive direction or a right drive direction while driving through the applied fluid in the alternating forward and reverse directions after spraying fluid on the floor surface; the method described above where fluid on the floor surface comprises spraying fluid in multiple positions with respect to the forward drive direction; the method described above where the second distance is at least equal to a length of one footprint area of the robot; the method described above where the mobile floor cleaning robot comprises: a robot body defining the forward drive direction and having a bottom portion, and a drive system supporting the robot body and configured to maneuver the robot over the floor surface.

One aspect of the disclosure provides a mobile robot having a robot body, a drive system, and a cleaning assembly. The cleaning assembly includes a pad holder, a fluid applicator and a controller. The drive system supports the robot body to maneuver the robot across a floor surface. The cleaning assembly is disposed on the robot body and includes a pad holder, a fluid applicator and a controller in communication with the drive system and the cleaning system. The pad holder is configured to receive a cleaning pad having a center and lateral edges. The pad holder includes a release mechanism configured to eject the pad upon actuation of a release mechanism. The fluid applicator is configured to apply fluid to the floor surface. The controller controls the drive system and fluid applicator while executing a cleaning routine. The cleaning routine includes applying fluid to an area substantially equal to a footprint area of the robot, and returning the robot to the area in a movement pattern that moves the center and lateral edges of the cleaning pad separately through the area to moisten the cleaning pad with the applied fluid.

Implementations of the disclosure may include one or more of the following features. In some implementations, the cleaning routine further includes applying fluid to the surface at an initial volumetric flow rate to moisten the cleaning pad, the initial volumetric flow rate being relatively higher than a subsequent volumetric flow rate when the cleaning pad is moistened. In one implementation, the first volumetric flow rate is set by spraying about 1 mL of fluid every 1.5 feet initially for a period of time such as 1-3 minutes, and the second volumetric flow rate is set by spraying every 3 feet, wherein each spray of fluid is less than 1 mL of volume.

In some examples, the fluid applicator applies fluid to an area in front of the cleaning pad and in the direction of travel of the mobile robot. In some examples, the fluid is applied to an area the cleaning pad has occupied previously. In some examples, the area the cleaning pad has occupied is recorded on a stored map that is accessible to the controller.

In some examples, the fluid applicator applies fluid to an area the robot has backed away from by a distance of at least one robot footprint length immediately prior to applying fluid. Executing the cleaning routine further comprises moving the cleaning pad in a birdsfoot motion forward and backward along a center trajectory, forward and backward along a trajectory to the left of and heading away from a starting point along the center trajectory, and forward and backward along a trajectory to the right of and heading away from a starting point along the center trajectory.

In some implementations, the drive system includes right and left drive wheels disposed on corresponding right and left portions of the robot body. A center of gravity of the robot is positioned forward of the drive wheels, causing a majority of an overall weight of the robot to be positioned over the pad holder. The overall weight of the robot 20 may be distributed between the pad holder and the drive wheels at a ratio of 3 to 1. In some examples, the overall weight of the robot is between about 2 lbs. and about 5 lbs.

In some examples, the robot body and the pad holder both define substantially rectangular foot prints. Additionally or alternatively, the bottom surface of the pad holder may have a width of between about 60 millimeters and about 80 millimeters and a length of between about 180 millimeters and about 215 millimeters.

In some implementations, the robot includes a toggle button for actuating the pad holder release mechanism and ejecting the pad. In some implementations, the pad includes a backing layer for engaging with the pad holder and the pad holder comprises raised protrusions positioned for aligning to and engaging with shaped slots cut out of the backing layer.

One aspect of the disclosure provides a mobile floor cleaning robot having a robot body, a drive, a cleaning assembly, a pad holder, and a controller circuit. The robot body defines a forward drive direction. The drive supports the robot body to maneuver the robot across a floor surface. The cleaning assembly is disposed on the robot body and includes a pad holder, a reservoir, and a sprayer. The pad holder has a bottom surface configured to receive a cleaning pad and arranged to engage the floor surface, and the bottom surface has one or more raised protrusions extending therefrom.

The one or more protrusions assist with aligning the pad to the pad holder and retaining the pad securely in place during oscillation of the orbital oscillation while the robot moves in a back and forth scrubbing cleaning pattern. In implementations, the pad holder includes a release mechanism configured to eject the pad from the bottom surface of the pad holder upon actuation of the release mechanism such that a user need not touch a used, dirty pad to dispose of it. Actuating the release mechanism while holding the robot above a trash container ejects the pad from the pad holder into the trash container therebeneath.

The reservoir is configured to hold a volume of fluid, and the sprayer, which is in fluid communication with the reservoir, is configured to spray the fluid along the forward drive direction forward of the pad holder. The controller circuit communicates with both the drive system and the cleaning system and executes a cleaning routine. The controller circuit executes a cleaning routine that allows the robot to drive in the forward drive direction a first distance to a first location and then drive in a reverse drive direction, opposite the forward drive direction, a second distance to a second location. The cleaning routine allows the robot to spray fluid on the floor surface from the second location, in the forward drive direction forward of the pad holder but rearward of the first location. In this manner, the robot only applies fluid to traversable floor and not to a wall, piece of furniture, carpet or other non-floor area that triggers a bump sensor (collision) switch or proximity sensor on the robot. After spraying fluid on the floor surface, the cleaning routine allows the robot to drive in alternating forward and reverse drive directions while smearing the cleaning pad along the floor surface.

Implementations of the disclosure may include one or more of the following features. In some implementations, the drive includes right and left drive wheels disposed on corresponding right and left portions of the robot body. A center of gravity of the robot is positioned forward of the drive wheels, causing a majority of an overall weight of the robot to be positioned over the pad holder. The overall weight of the robot may be distributed between the pad holder and the drive wheels at a ratio of 3 to 1. In some examples, the overall weight of the robot is between about 2 lbs. and about 5 lbs (about 1 to 2.25 kg). The drive may include a drive body, which has forward and rearward portions, and right and left motors disposed on the drive body. The right and left drive wheels may be coupled to the corresponding right and left motors. The drive system may also include an arm that extends from the forward portion of the drive body. The arm is pivotally attachable to the robot body forward of the drive wheels to allow the drive wheels to move vertically with respect to the floor surface. The rearward portion of the drive body may define a slot sized to slidably receive a guide protrusion extending from the robot body.

In some examples, the robot body and the pad holder both define substantially rectangular foot prints. Additionally or alternatively, the bottom surface of the pad holder may have a width of between about 60 millimeters and about 80 millimeters and a length of between about 180 millimeters and about 215 millimeters.

The reservoir may hold a fluid volume of about 200 milliliters. Additionally or alternatively, the robot may include a vibration motor, or orbital oscillator, disposed on the top portion of the pad holder.

In some implementations, the robot includes a toggle button for actuating the pad holder release mechanism and ejecting the pad. In some implementations, the pad includes a backing layer for engaging with the pad holder and the pad holder comprises raised protrusions positioned for aligning to and engaging with shaped slots cut out of the backing layer.

Another aspect of the disclosure provides a mobile floor cleaning robot that includes a robot body, a drive, and a cleaning assembly. The robot body defines a forward drive direction. The drive system supports the robot body to maneuver the robot across a floor surface. The cleaning assembly is disposed on the robot body and includes a pad holder and an orbital oscillator. The pad holder is disposed forward of the drive wheels and has a top portion and a bottom portion. The bottom portion has a bottom surface arranged within between about 0.5 cm and about 1.5 cm of the floor surface and receives a cleaning pad. The bottom surface of the pad holder includes at least 40 percent of a surface area of a footprint of the robot and has one or more raised protrusions extending therefrom. The orbital oscillator is disposed on the top portion of the pad holder and has an orbital range less than 1 cm. The pad holder is configured to permit more than 80 percent of the orbital range of the orbital oscillator to be transmitted from the top of the held cleaning pad to the bottom surface of the held cleaning pad.

In some examples, the orbital range of the orbital oscillator is less than ½ cm during at least part of a cleaning run. Additionally or alternatively, the robot may move the cleaning pad forward or backward while the cleaning pad is oscillating.

The one or more protrusions assist with aligning the pad to the pad holder and retaining the pad securely in place during oscillation of the orbital oscillation while the robot moves in a back and forth scrubbing cleaning pattern. In implementations, the pad holder includes a release mechanism configured to eject the pad from the bottom surface of the pad holder upon actuation of the release mechanism such that a user need not touch a used, dirty pad to dispose of it. Actuating the release mechanism while holding the robot above a trash container ejects the pad from the pad holder into the trash container therebeneath.

In some examples, the robot moves in a birdsfoot motion forward and backward along a center trajectory, forward and backward along a trajectory to the left of and heading away from a starting point along the center trajectory, and forward and backward along a trajectory to the right of and heading away from a starting point along the center trajectory.

In some examples, the cleaning pad has a top surface attached to the bottom surface of the pad holder and the top of the pad is substantially immobile relative to the oscillating pad holder.

In some examples, the pad holder has a release mechanism configured to eject the pad from the bottom surface of the pad holder upon actuation of a release mechanism. In some examples, robot includes a toggle button for actuating the pad holder release mechanism and ejecting the pad. In some examples, the pad includes a backing layer for engaging with the pad holder and the pad holder comprises raised protrusions positioned for aligning to and engaging with shaped slots cut out of the backing layer.

In some examples, the overall weight of the robot is distributed between the pad holder and the drive wheels at a ratio of 3 to 1. The overall weight of the robot may be between about 2 lbs. and about 5 lbs (about 1 to 2.25 kg).

In some examples, the robot body and the pad holder both define substantially rectangular foot prints. Additionally or alternatively, the bottom surface of the pad holder may have a width of between about 60 millimeters and about 80 millimeters and a length of between about 180 millimeters and about 215 millimeters.

The cleaning assembly may further include at least one post disposed on the top portion of the pad holder sized for receipt by a corresponding aperture defined by the robot body. The at least one post may have a cross sectional diameter varying in size along its length. Additionally or alternatively, the at least one post may include a vibration dampening material.

In some implementations, the cleaning assembly further includes a reservoir to hold a volume of fluid, and a sprayer in fluid communication with the reservoir. The sprayer is configured to spray the fluid along the forward drive direction forward of the pad holder. The reservoir may hold a fluid volume of about 200 milliliters.

The drive may include a drive body, which has forward and rearward portions, and right and left motors disposed on the drive body. The right and left drive wheels are coupled to the corresponding right and left motors. The drive may also include an arm that extends from the forward portion of the drive body. The arm is pivotally attachable to the robot body forward of the drive wheels to allow the drive wheels to move vertically with respect to the floor surface. The rearward portion of the drive body may define a slot sized to slidably receive a guide protrusion that extends from the robot body. In one implementation, the cleaning pad disposed on the bottom surface of the pad holder body absorbs about 90% of the fluid volume held in the reservoir. The cleaning pad has a thickness of between about 6.5 millimeters and about 8.5 millimeters, a width of between about 80 millimeters and about 68 millimeters, and a length of between about 200 millimeters and about 212 millimeters.

In some examples, a method includes driving a first distance in a forward drive direction defined by the robot to a first location, while moving a cleaning pad carried by the robot along a floor surface supporting the robot. The cleaning pad has a center area and lateral areas flanking the center area. The method further includes driving in a reverse drive direction opposite the forward drive direction, a second distance to a second location while moving the cleaning pad along the floor surface In this manner, the robot only applies fluid to traversable floor and not to a wall, piece of furniture, carpet or other non-floor area that triggers a bump sensor (collision) switch or proximity sensor on the robot. The method also includes applying fluid to an area on the floor surface substantially equal to a footprint area of the robot and forward of the cleaning pad but rearward of the first location. The method further includes returning the robot to the area of applied fluid in a movement pattern that moves the center and lateral portions of the cleaning pad separately through the area to moisten the cleaning pad with the applied fluid.

In some examples, the method includes driving in a left drive direction or a right drive direction while driving in the alternating forward and reverse directions after spraying fluid on the floor surface. Applying fluid on the floor surface may include spraying fluid in multiple directions with respect to the forward drive direction. In some examples, the second distance is at least equal to the length of a footprint area of the robot.

In still yet another aspect of the disclosure, a method of operating a mobile floor cleaning robot includes driving a first distance in a forward drive direction defined by the robot to a first location while smearing a cleaning pad carried by the robot along a floor surface supporting the robot. The method includes driving in a reverse drive direction, opposite the forward drive direction, a second distance to a second location while smearing the cleaning pad along the floor surface. The method also includes spraying fluid on the floor surface in the forward drive direction forward of the cleaning pad but rearward of the first location. The method also includes driving in an alternating forward and reverse drive directions while smearing the cleaning pad along the floor surface after spraying fluid on the floor surface.

In some implementations, the method includes spraying fluid on the floor surface while driving in the reverse direction or after having driven in the reverse drive direction the second distance. In implementations, the he method includes driving in a left drive direction or a right drive direction while driving in the alternating forward and reverse directions after spraying fluid on the floor surface.

Spraying fluid on the floor surface may include spraying fluid in multiple directions with respect to the forward drive direction. In some implementations, the second distance is greater than or equal to the first distance.

The mobile floor cleaning robot may include a robot body, a drive, a pad holder, a reservoir, and a sprayer. The robot body defines the forward drive direction and has a bottom portion. The drive system supports the robot body and maneuvers the robot over the floor surface. The pad holder is disposed on the bottom portion of the robot body and holds the cleaning pad. The pad holder has a release mechanism configured to eject the pad upon actuation, and the pad further comprising a backing layer for engaging with the pad holder. The pad holder has a bottom surface having raised protrusions extending therefrom and the raised protrusions are sized, shaped and positioned to align to and engage with slots cut out of the backing layer.

The reservoir is housed by the robot body and holds a fluid (e.g., 200 ml). The sprayer, which is also housed by the robot body, is in fluid communication with the reservoir and sprays the fluid in the forward drive direction forward of the cleaning pad. The cleaning pad disposed on the bottom portion of the pad holder may absorb about 90% of the fluid contained in the reservoir. In some examples, the cleaning pad has a width of between about 80 millimeters and about 68 millimeters and a length of between about 200 millimeters and about 212 millimeters. The cleaning pad may have a thickness of between about 6.5 millimeters and about 8.5 millimeters. The details of one or more implementations of the disclosure are set forth in the accompanying drawings and the description below.

In some implementations, the fluid applicator is a sprayer that includes at least two nozzles each distributing the fluid evenly across the floor surface in two strips of applied fluid. The two nozzles are each configured to spray the fluid at an angle and distance different than another nozzle. In some implementations, the two nozzles are vertically stacked in a recess in the fluid applicator and angled from horizontal and spaced apart from one another such that one nozzle sprays relatively longer lengths of fluid forward and downward to cover an area in front of the robot with a forward supply of applied fluid 173*a*, and the other nozzle sprays relatively shorter lengths fluid forward and downward to leave a rearward supply of applied fluid on an area in front of but closer to the robot than the area of applied fluid dispensed by the top nozzle.

In implementations, the nozzle or nozzles dispense fluid in an area pattern that extends one robot width and at least one robot length in dimension. In some implementations, the top nozzle and bottom nozzle apply fluid in two distinct spaced apart strips of applied fluid that do not extend to the full width of the robot such that the pad passes through the outer edges of the strips of applied fluid in forward and backward angled scrubbing motions as described herein. In embodiments, the strips of applied fluid cover a width of 75-95% of the robot width and a combined length of the robot length. In implementations, the strips of applied fluid may be substantially rectangular shaped or ellipse shaped. In implementations, the nozzles complete each spray cycle by sucking in a small volume of fluid at the opening of the nozzle so that no fluid leaks from the nozzle following each instance of spraying.

In some implementations, the pad includes a cardboard backing layer adhered to the top surface of the pad. The cardboard backing layer protrudes beyond the longitudinal edges of the pad and the protruding longitudinal edges of the cardboard backing layer attach to the pad holder of the robot.

In one embodiment, the cardboard backing layer is between 0.02 inch and 0.03 inch thick (0.05 cm and 0.762 cm thick), between 68 and 72 mm wide and between 90-94 mm long. In one embodiment, the cardboard backing layer 85 is 0.026 inch thick, 70 mm wide and 92 mm long. In one embodiment, the cardboard backing layer is coated on both sides with a water resistant coating, such as wax or polymer or a combination of water resistant materials, such as wax/polyvinyl alcohol/polyamine, and the cardboard backing layer does not disintegrate when wetted.

In implementations, the pad is a disposable pad. In other examples, the pad is a reusable microfiber cloth pad having the same absorptive characteristics as those described herein with regard to embodiments. In examples having a washable, reusable microfiber cloth, the top surface of the cloth includes a secured stiff backing layer shaped and positioned like the cardboard backing layer described with regard to embodiments. The stiff backing layer is made of heat resistant, washable material that withstands being machine dried without melting or degrading the backing. The stiff backing layer is dimensioned and has cutouts as described herein for interchangeable use with the embodiment of the pad holder described with regard to embodiments herein.

In other examples, the pad is a disposable dry cloth and comprises a single layer of needle punched spunbond or spunlace material having exposed fibers for entrapping hair. The dry pad further comprises a chemical treatment that adds a tackiness characteristic to the pad for retaining dirt and debris. In one embodiment, the chemical treatment is a material such as that marketed under the trade name DRAKESOL.

In some examples, the pad is secured to an autonomous robot through a pad holder attached to the robot. A pad release mechanism adjusts to an up or pad-secure position. The pad release mechanism includes a retainer, or lip, that holds the pad securely in place by grasping protruding longitudinal edges of a cardboard backing layer secured to the top of the pad. In examples, the tip or end of the pad release mechanism includes a moveable retention clip and an eject protrusion that slides up through a slot or opening in the pad holder, and is pushed through the slot into a down position to release the secured pad by pushing down on the attached cardboard backing layer.

Other aspects, features, and advantages will be apparent from the description and drawings, and from the claims.

DESCRIPTION OF DRAWINGS

FIG. 8A is a perspective view of an exemplary cleaning pad.

FIG. 8B is an exploded perspective view of the exemplary cleaning pad of FIG. 8A.

FIG. 8C is a top view of an exemplary cleaning pad.

FIG. 8D is a bottom view of an exemplary attachment mechanism for the pad as described herein.

Like reference symbols in the various drawings indicate like elements.

DETAILED DESCRIPTION

Figure 1A:
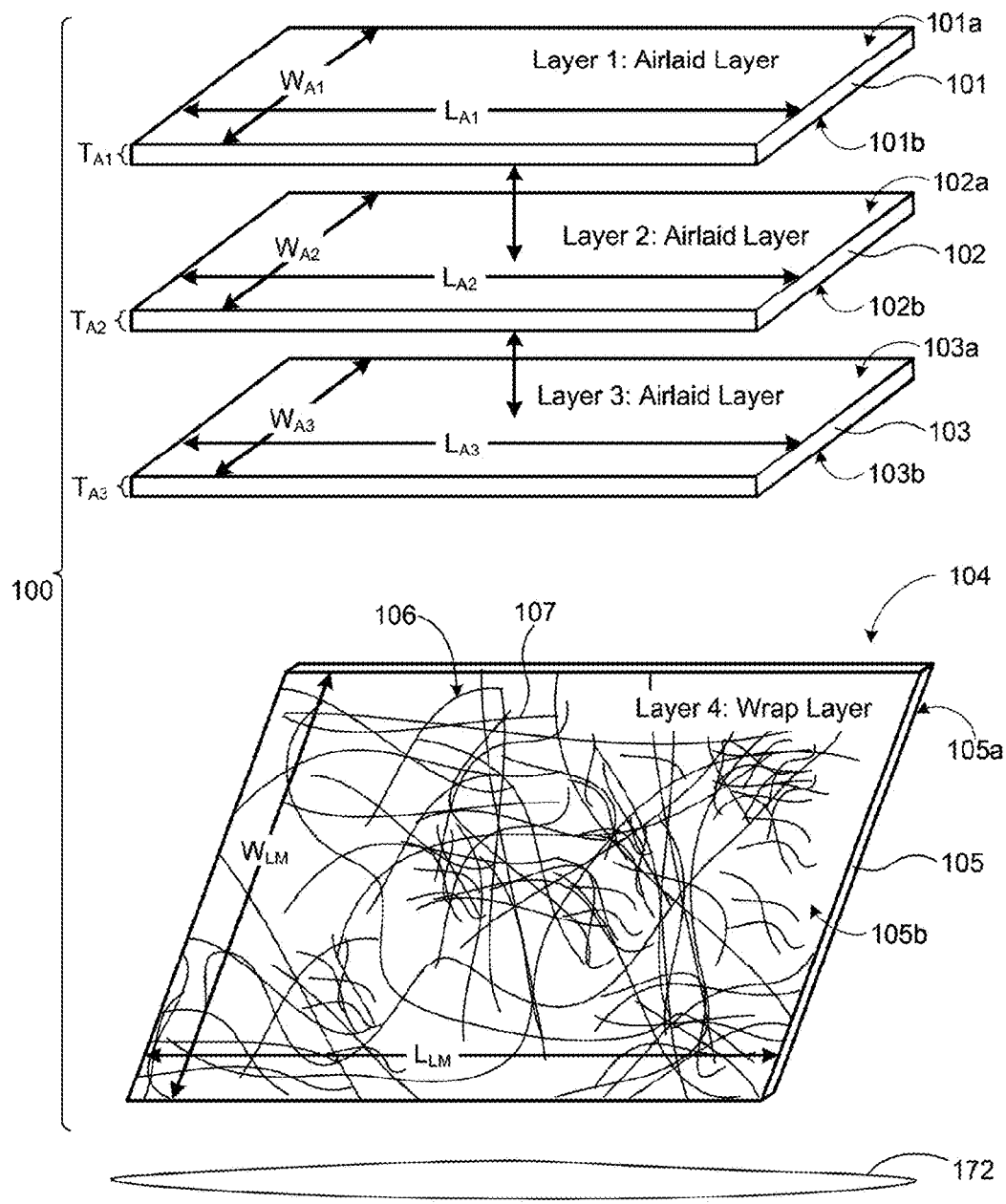
FIG. 1A is an exploded view of an exemplary cleaning pad.
Figure 1B:
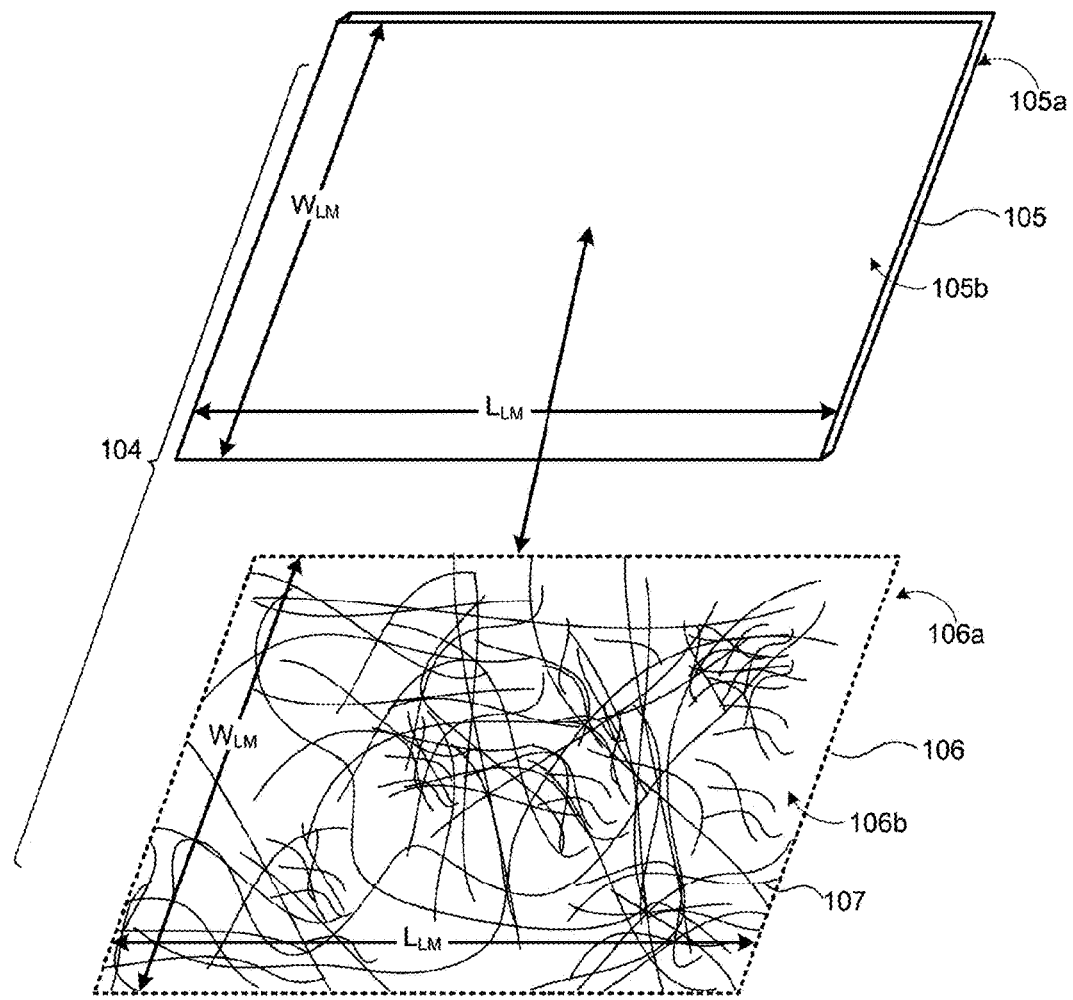
FIG. 1B is an exploded view of the wrap layer of the exemplary cleaning pad of FIG. 1.
Figure 1C:
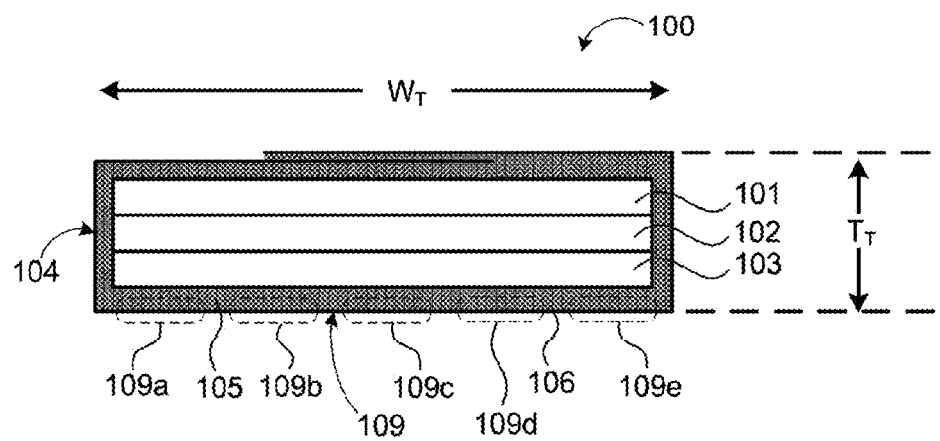
FIG. 1C is a section view of an exemplary cleaning pad.

Referring to FIGS. 1A, 1B and 1C, in some implementations, a disposable cleaning pad 100 includes a plurality of absorbent airlaid layers 101, 102, 103 stacked, optionally bonded to one another, and enwrapped by an outer nonwoven layer 105 which can have an abrasive meltblown elements 106 disposed thereon. In some examples, the cleaning pad 100 includes one or more airlaid layers 101, 102, 103. As shown, the cleaning pad 100 includes first, second and third airlaid layers 101, 102, 103, but additional airlaid layers are possible as well. The number of airlaid layers 101, 102, 103 may depend on the amount of cleaning fluid 172 the cleaning pad 100 is required to absorb. Each airlaid layer 101, 102, 103 has a top surface 101a, 102a, 103a and a bottom surface 101b, 102b, 103b. The bottom surface 101b of the first (or top) airlaid layer 101 is disposed on the top surface 102a of the second airlaid layer 102, and the bottom surface 102b of the second airlaid layer 102 is disposed on the top surface 103a of the third (or bottom) airlaid layer 103. Fluid wicks between the three layers and is retained uniformly vertically throughout the stack of airlaid layers without leaking back onto a floor surface beneath the cleaning pad 100 while downward force is applied to the pad 100. In implementations, the pad 100 retains 90 percent of fluid applied to a floor surface 10 and under 1 pound of force, the pad 100 does not leak absorbed fluid back onto the floor surface 10. The surface tension the top and bottom surfaces of each airlaid layer helps retain wicked fluid within each layer such that as the top layer 101 fully saturates, no fluid will leak down to the middle airlaid layer 102 through the bottom surface 101b of the top airlaid layer 101, and as the middle airlaid layer 102 fully saturates, no fluid will leak down to the bottom layer through the bottom surface 102b of the middle (or second) layer 102.

In implementations, the pad 100 soaks up 8-10 times its weight into a relatively rigid matrix of airlaid layers 101, 102, 103, and fluid absorption is achieved through capillary wicking, not by compress-release drawing because robot 400 to which the pad is attached exerts very light, low variability cycle weight, not a cycle of heavy human push down and draw back. Each of airlaid layer 101, 102, 103 slows down penetration of wicked fluid to the next adjacent airlaid layer 101, 102, 103, such that early cycles of fluid application do not lead to the pay quickly sopping up all the fluid that is applied to the floor surface. The vertical stack of airlaid layers 101, 102, 103 provides a resistance to puddling at the bottom of the airlaid core comprising the three airlaid layers 101, 102, 103. Each of the of airlaid layers 101, 102, 103 has its own puddle resisting bottom surface 101b, 102b, 103b for preventing puddling of absorbed fluid all the way down at the bottom of the bottom surface 103b of the bottom (or third) layer 103b.

In embodiments, the airlaid layers 101, 102, 103 are of non-uniform hardness or density in the vertically direction such the outer top and bottom surfaces are harder than the interior of each layer. In embodiments, the airlaid layers 101, 102, 103 are of non-uniform surface density such that the outer top and bottom surfaces are smoother and less absorptive than the interior of each layer. By varying the surface density at the outer surfaces 101b, 102b, 103b of each of the airlaid layer 101, 102, 103, the airlaid layers 101, 102, 103 remain absorptive, wicking fluid into each airlaid layer without leaking back through the bottom surfaces 101b, 102b, 103b. By incorporating three such airlaid layers 101, 102, 103 into the absorptive core of the pad 100, the pad 100 therefore has superior fluid retention properties over a pad having a single core of thickness equivalent to the three layer stacked core. The three airlaid layers 101, 102, 103 provide at least triple the amount of surface tension for retaining wicked fluid in the absorptive cores of each of the airlaid layers 101, 102, 103.

A wrap layer 104 wraps around the airlaid layers 101, 102, 103 and prevents the airlaid layers 101, 102, 103 from being exposed. The wrap layer 104 includes a wrap layer 105 (e.g., a spunlace layer) and an abrasive layer 106. The wrap layer 105 is wrapped around the first, second, and third airlaid layers 101, 102, 103. The wrap layer 105 has a top surface 105a and a bottom surface 105b. The top surface 105b of the wrap layer 105 covers the airlaid layers 101, 102, 103. The wrap layer 105 may be a flexible material having natural or artificial fibers (e.g., spunlace or spunbond). The abrasive layer 106 is disposed on the bottom side 105b of the wrap layer 105. Fluid applied to a floor 10 beneath the cleaning pad 100 transfers through the wrap layer 105 and into the airlaid layers 101, 102, 103. The wrap layer 105 wrapped around the airlaid layers 101, 102, 103 is a transfer layer that prevents exposure of raw absorbent material in the airlaid layers. If the wrap layer 105 were too absorbent, the pad 100 would be suctioned onto a floor 10 and difficult to move. A robot, for example, may be unable to overcome the suction force while trying to move the cleaning pad 100 across the floor surface 10. Additionally, the wrap layer 105 picks up dirt and debris loosened by the abrasion outer layer 106 and may leave a thin sheen of a cleaning fluid 172 on the surface 10 that air dries without leaving streak marks on the floor 10. The thin sheen of cleaning solution is between 1.5 and 3.5 ml/square meter and dries in a duration no longer than three minutes, and preferably dries within between about 2 minutes and 3 minutes.

The disposable cleaning pad 100 relies on capillary action (also known as wicking) to absorb fluid on a floor surface 10.

Capillary action occurs when a liquid is able to flow in narrow spaces without external forces, such as gravity. Capillary action allows a fluid to move within spaces of a porous material due to forces of adhesion, cohesion, and surface tension. Adhesion of the fluid to the walls of a vessel will cause an upward force on the liquid edges and result in meniscus, which turns upwards. The surface tension acts to hold the surface intact. Capillary action occurs when the adhesion to the walls is stronger than the cohesive forces between the fluid molecules.

In some examples, the airlaid layers 101, 102, 103 are a textile-like material made from fluff pulp, which is a type of wood pulp/chemical pulp made from long fiber softwoods. Chemical pulp is created by applying heat to a combination of wood chips and chemical materials in a large container to break down the lignin (organic substance that binds the cells in the wood). The textile-like material that is made from fluff pulp may be very bulky, porous, soft, and has good water absorption properties. The textile-like material does not scratch the floor surface, maintains its strength even when it is wet, and may be washed and reused.

Figure 1D:
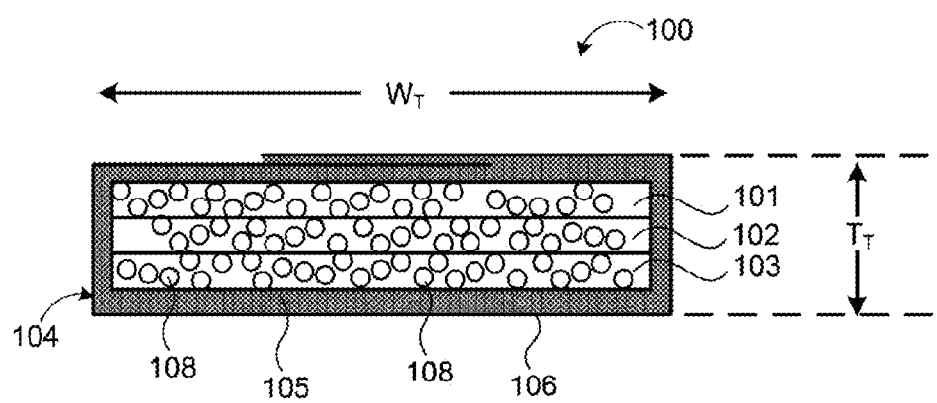
FIG. 1D is a section view of an exemplary cleaning pad where the airlaid layers include superabsorbent polymers.

Referring to FIG. 1D, in some implementations, the airlaid layers 101, 102, 103 include an absorbent layer of a mixture of air-laid paper and superabsorbent polymers 108 (e.g., sodium polyacrylate) for wetness. Polymers include plastic and rubber materials, which are mainly organic compounds that are chemically based on carbon, hydrogen, and other nonmetallic elements. Polymers generally have larger molecular structures, which typically have low densities and may be extremely flexible. Superabsorbent polymers 108 (also known as slush powder) absorb and retain large amounts of a fluid in comparison to their own mass. The ability of the superabsorbent polymers 108 to absorb water depends on the ionic concentration of the aqueous solution. A superabsorbent polymer 108 may absorb up to 500 times its weight in deionized and distilled water (30-60 times its volume) and may become 99.9% liquid. The absorbency of the superabsorbent polymers 108 drops significantly to about 50 times its weight when put into a 0.9% saline solution. The valence cations in the saline solution prevent the superabsorbent polymer 108 from bonding with the water molecules. The superabsorbent polymers 108 may expand causing the cleaning pad 100 to expand as well. Various implements 400, 500 may use the cleaning pad 100, and, in some examples, the implements 400, 500 may not support a cleaning pad 100 that may expand. For example, expansion of the pad 100 may disturb the physics of a compact, lightweight robot 400, causing the compact robot 400 to tilt upward and apply less force to the pad 100 for debris removal from the floor 10. Therefore, less superabsorbent polymers 108 may be used to meet a cleaning pad absorbency requirement. In one embodiment, the pad 100 may contain pockets in a middle section along the pad length that allow superabsorbent polymers to expand into those pockets and allow the pad to maintain a constant thickness as the superabsorbent polymers expand.

In some implementations, the airlaid layers 101, 102, 103 include a cellulose pulp nonwoven material that is through air bonded with a bicomponent fiber. In some examples, fibers of wood pulp cellulose are thermally bonded with bicomponent polyethylene, and/or polypropylene, which has a low melting point. This mixture forms a solid absorbent core that holds its formed shape and that evenly distributes absorbed fluid, preventing cleaning fluid from pooling at the lowest point in the layer and preventing additional fluid accumulation. The airlaid layers 101, 102, 103 may be manufactured from a bleached wood pulp that looks like a thick layer of cardboard. The pulp enters a hammer mill having blades on a rotor that strikes the thick layer of pulp and devibrates it into individual fibers. The individual fibers enter a distributor having a screen rotor that looks like a flour sifter. The fibers are formed into a sheet on another screen having an applied vacuum underneath, at which stage the sheet is blended with a sheet of bicomponent fiber. Blown hot air melts the bicomponent to bond with the airlaid.

The airlaid layers are situated so as to distribute the absorbed liquid substantially uniformly throughout the core, without puddling of liquid anywhere in the core layers (expand?). The mobile robot 400 sprays fluid 172 in front of the robot uniformly and the pad 100 picks up the applied solution 173a, 173b in an even distribution along its length when traveling forward. In one embodiment, the airlayed layers 101, 102, 103 are bonded with spray adhesive applied evenly over the surface of the airlaid layer 101, 102, 103. In one embodiment, the adhesive is polyolefin and is applied in a thin, uniform manner to get reliable adhesion without creating ridges and stiff areas. The spray adhesive also creates a uniformly bonded surface interface, allows fluid to wick into the airlaid layers 101, 102, 103 without a large mechanical barrier (for example, stitches, or relatively large impermeable glue patches or ridges) and this uniformly bonded surface interface between airlaid layers 101, 102, 103 prevents puddling between the layers 101, 102, 103.

A very small amount of acrylic latex bonding agent may be sprayed sparingly on both the surfaces to bind the external layers and to minimize sloughing and help reduce linting. Linting is a condition that occurs when fine ravelings of cotton, linen, or fiber are apparent on an object or fabric. The airlaid layers 101, 102, 103 may include 15% of biocomponent polymers, 85% cellulose, and latex at the top to eliminate linting.

The wrap layer 105 may be of any material that is thin and absorbs fluid. In addition, the wrap layer 105 may be smooth to prevent scratching the floor surface 10. In some implementations, the cleaning pad 100 may include one or more of the following cleaning agent constituents butoxypropanol, alkyl polyglycoside, dialkyl dimethyl ammonium chloride, polyoxyethylene castor oil, linear alkylbenzene sulfonate, glycolic acid—which for example serve as surfactants, and to attack scale and mineral deposits, among other things; and including scent, antibacterial or antifungal preservatives.

In some examples, the wrap layer 105 is a spunlace nonwoven material. Spunlace may also be known as hydroentangling, water entangling, jet entangling or hydraulic needling. Spunlace is a process of entangling a web of loose fibers typically formed by a card on a porous belt or moving perforated or patterned screen to form a sheet structure by subjecting the fibers to multiple passes of fine high-pressure water jets. The hydroentangling process enables formation of specialty fabrics by adding fibrous materials, such as tissue paper, airlaid, spunlace and spunbond nonwovens to composite non-woven webs. These materials offer performance advantages needed for many wipe applications due to their improved performance or cost structure.

Figure 2A:
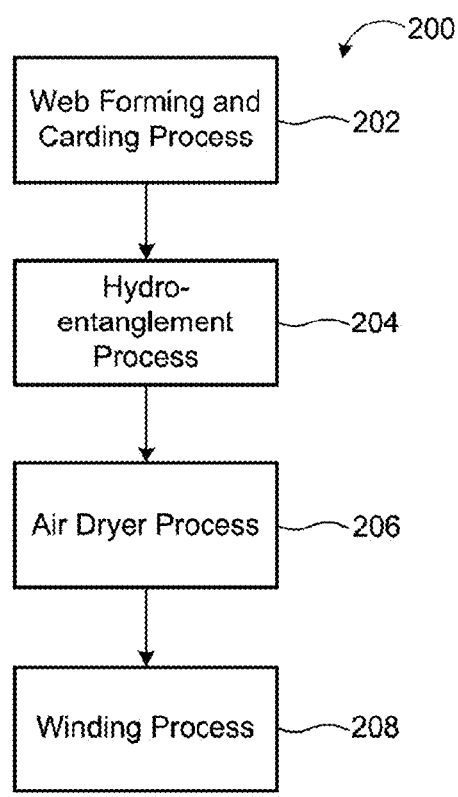
FIG. 2A is a schematic view of an exemplary arrangement of operations for a spunlace process.
Figure 2B:
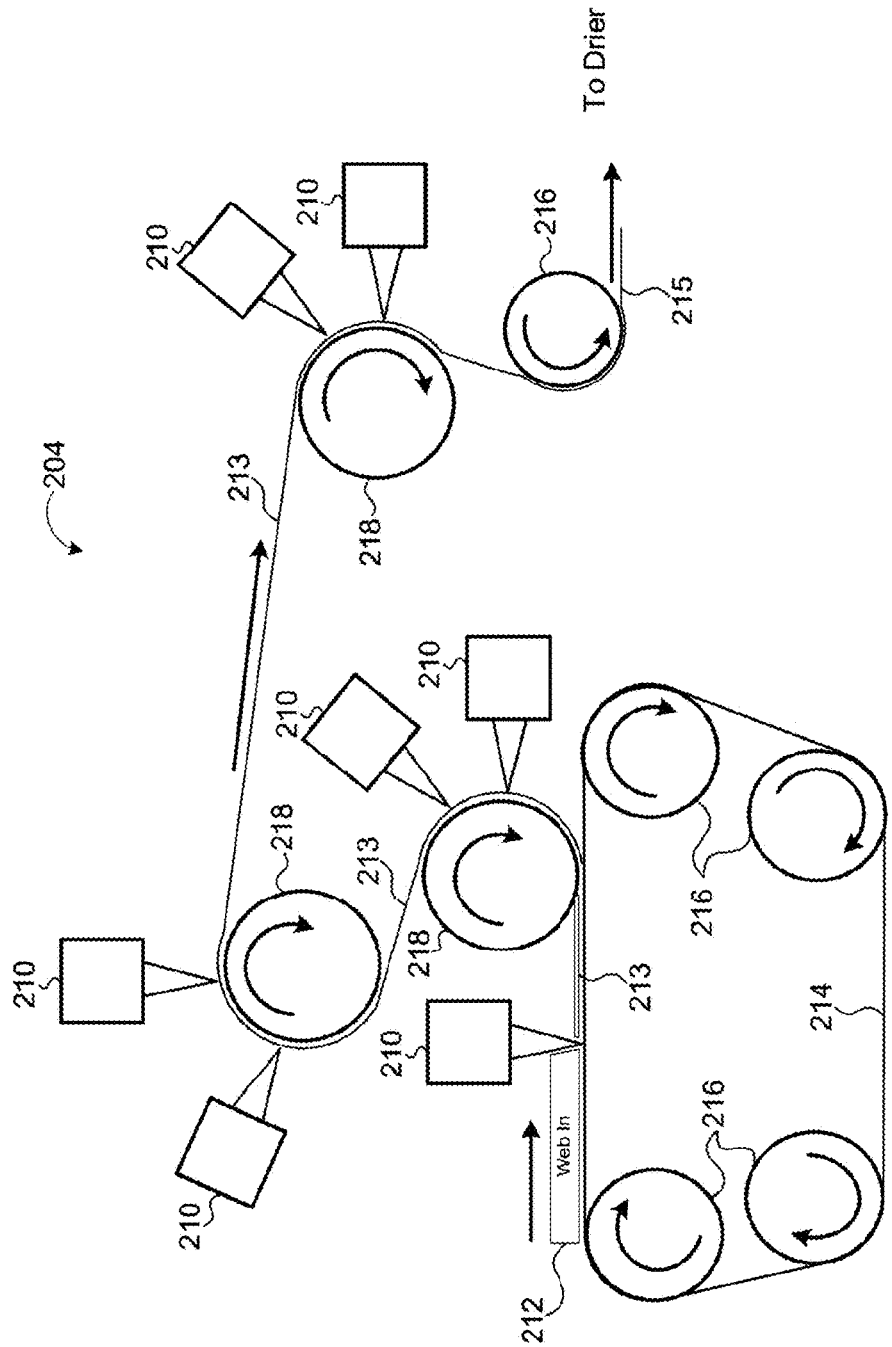
FIG. 2B is a perspective view of the hydroentaglement process for making the spunlace layer used in the exemplary cleaning pad.

Referring to FIGS. 2A and 2B, the spunlace process 200 includes a precursor web forming process 202a. The precursor web is usually made of staple textile-like fibers. These webs can be single fiber webs or made of many different fiber blends. The typical four fibers of choice are polyester, viscose, polypropylene and cotton. Variants of each of these fibers may also be used, such as organic cotton, as well as Lyocell material, and Tencel rayon. PLA (polylactic acid) fibers which are biodegradable can also be used.

The precursor web forming process 202a may include forming airlaid cards, which may be used to provide a more isotropic web as a result of higher transversal orientation of the fibers. Carding is a method of making thin webs of parallelized fibers. Higher bulk may also be obtained by using this type of carding system. Once the web of staple fibers is formed, a second layer of fibers may be placed on top of this base by air forming cellulose fibers, or by "laminating" a pre-formed nonwoven web, such as tissue, spunlace or spunbond. In some examples, spunbond isisnonwoven material is combined is combined with airlaid layers and thus the resulting fabric eliminates the carding step of hydroentangling continuous fibers with cellulose pulp fibers. This fibrous composition then goes under a fiber entangling process 204 constituted of rows of high-pressure water jets 210 that duplicate the conventional mechanical needling process and intertwine the fibers individually, so that they become entangled forming a web 212.

The spunlace process 200 includes applying a fiber entangling process 204 to the fibrous composition. The fiber entangling process 204 includes jetting water from rows of high-pressure water jets 210 to duplicate the conventional mechanical needling process and intertwine the fibers individually so that they become entangled, forming a web 212. The web 212 (after going through the web forming and carding process 202) is placed on a conveyor belt 214 rotated by two or more pulleys 216. During and/or after each water injection process the web 212 goes through drums with suction 218 that suck the water out of the fiber and allow the fiber to keep moving to the next high-pressure water jets 210.

The consolidated nonwoven substrate 215 is subsequently dried through air-dryers in an air dryer process 206 and then wound in a winding process 208.

The wrap layer 105 can be printed on as well as thermally embossed. Embossing and debosing are processes for creating raised or recessed designs in fabric or other material. A relatively lower melt fiber, such as polypropylene, may be used to achieve better thermal embossing. The coefficient of friction of the wrap layer 105 varies based on surface type and wetness. In on embodiment, a dry pad 100 moving on glass has a coefficient of friction of about 0.4 to about 0.5, and wet on tiles has a coefficient of friction of about 0.25 to about 0.4. The wrap layer 105 may include hydroembossing, which imparts three dimensional images on the fabric. Hydroembossing is generally less expensive than thermal bonding. In one example, the wrap layer 105 is embossed with a herringbone pattern. The wrap layer 105 wrapped around a series of airlaid layers 101, 102, 103 enables the formation of an absorbent core that locks in absorbed fluid. The layering of airlaid core layers 101, 102, 103 enables capillary action and retention throughout the combined core and within each individual layer 101,102, 103. Furthermore, the airlaid layers 101, 102, 103 making up the core of the pad retain their shape while distributing fluid evenly throughout each fluid retention layer and preventing pooling that would prohibit additional absorption.

The abrasion meltblown layer 106 includes meltblown fibers 107, which are fibers formed by extruding a molten thermoplastic material through a plurality of fine, usually circular, die capillaries as molten threads or filaments into converging high velocity gas streams that cut the filaments of molten thermoplastic material to reduce their diameters. Thus, the meltblown fibers 107 are carried by the high velocity gas stream and placed on a surface that collects the fibers, therefore forming a web of randomly distributed meltblown fibers 107.

In some examples, the abrasion meltblown layer 106 is a layer of meltblown fibers 107 that provide a rough surface. The meltblown fibers 107 are formed by a meltblown process 300 (see FIG. 3) at high throughput, which creates spittle, or hair like fibers, that are formed by a polymer drooled from the die orifices due to temperature and other conditions in which it is run. The abrasive layer 106 is formed on top of the wrap layer 105 (e.g., another meltblown layer, a spunbond layer, or a spunlace layer). The wrap layer 105 may be a herring bone hydroembossed nonwoven material, which is made of a ratio of viscose (rayon) fibers blended with polyester fibers. In some examples, the abrasion meltblown layer 106 has a basis weight (also known as grammage) equal to 55 g/m$^2$ (grams per square meter). The wrap layer 105 may have a basis weight of between about 30 gsm (grams per square meter) and about 65 gsm. In other examples, the wrap layer may have a basis weight of between about 35-40 gsm. Basis weight is a measurement used in both the fabric and paper industries to measure the mass of the product per unit of area. In an embodiment, the wrap layer 105 is a hydroentangled spunbond or spunlace material formed with indentations (not show) therein that allow fluid and suspended dirt to pass more directly through to the airlaid layers 101, 102, 103 and reduce the amount of cohesive suction between the wrap layer 105 and the floor surface 10 when the pad 100 is wet. In one embodiment, the indentations are in a herringbone pattern. In another embodiment, the indentations form a grid of squares sized and spaced to be between 0.50 and 1.0 mm square and spaced apart in a grid formation by a length of 2.0-2.5 mm. In one embodiment, the indentations are sized and spaced to be 0.75 mm square and spaced apart in a grid formation by a length of 2.25 mm. In another embodiment, the wrap layer 105 is a spunbond or spunlace material having needle-punched holes therein for improving the wicking ability of the wrap layer 105 and decreasing the cohesion between the wet wrap layer 105 and the floor surface 10. The herringbone, square and needle punched indentations prevent a negative pressure from generating at the outside of the wrap layer as fluid evaporates and/or wicks from the back of the liner. Without free movement inside the wrap layer 105 or some texture on the wrap layer 105, fluid applied to the floor surface 10 cannot replace the wicked fluid, and that causes suction between the pad 100 and the floor. Combining a low density spunbond or spunlace material of 35-40 gsm with a surface texture in the form of hydroembossed indentations, surface textures and patterns (such as herringbone), or needle punched indentations or holes prevents suction between the pad and the floor. The meltblown layer 105 further assists with preventing this this suction force.

Additionally, when a pad 100 is damp, not enough fluid is present to lubricate the interface between the bottom surface of the pad and the floor surface 10. A fully wetted pad 100 will ride on a layer of fluid while the robot 400 is moving, but as the damp pad 100 slowly absorbs fluid, the not fully wet, not fully lubricated, wrap layer 106 will drag on the floor surface 10. In implementations, the spunbond or spunlace wrap layer 105 is manufactured with hydrophilic fibers that minimize the surface area of the pad 100 exposed to air between the pad 100 and the floor surface 10. A wet pad 100 would stick to the hydrophilic floor surface 10 if the indentations or needle punches were not part of the wrap layer 100. Applying a surface texture to the spunbond or spunlace of the wrap layer 105 breaks the surface tension that would otherwise case a wet pad 100 to stick to a wet floor surface 10.

The weight of the abrasion meltblown layer 106 is such that the abrasion meltblown layer 106 acts as an absorbing layer and allows for fluid to be absorbed through the meltblown layer 106 and be retained by the airlaid layer 101, 102, 103. In some examples, the meltblown layer 106 covers about 60 to about 70% of the surface area of the spunlace wrap layer 105 and in other examples, the meltblown layer 106 covers about 50-60% of the surface area of a spunbond or spunlace wrap layer 105.

The meltblown fibers 107 may have different arrangements and configurations on the spunlace wrap layer 105. In some examples, the meltblown fibers 107 are randomly arranged on the wrap layer 105. The meltblown fibers 107 may be arranged in one or more sections 109a-e on a cleaning surface 109. The cleaning surface 109 is a bottom surface of the cleaning pad 100 that is in contact with the floor surface 10. The one or more sections 109a-e on the cleaning surface 109 have a covered ratio between the meltblown abrasive fibers 107 and the wrap layer 105 greater than 50%. The meltblown layer provides the pad with the advantages of breaking surface tension that might otherwise cause the wet wrap layer to stick to a wet floor. By adding texture and topography to a floor facing surface of the pad, the meltblown layer prevents the pad from sticking or encountering high drag forces. The meltblown layer also provides the pad with surface texture for roughing up dirt and debris stuck or dried to a floor surface and loosening dirt and debris for absorption by the airlaid inner core of the pad.

Figure 3:
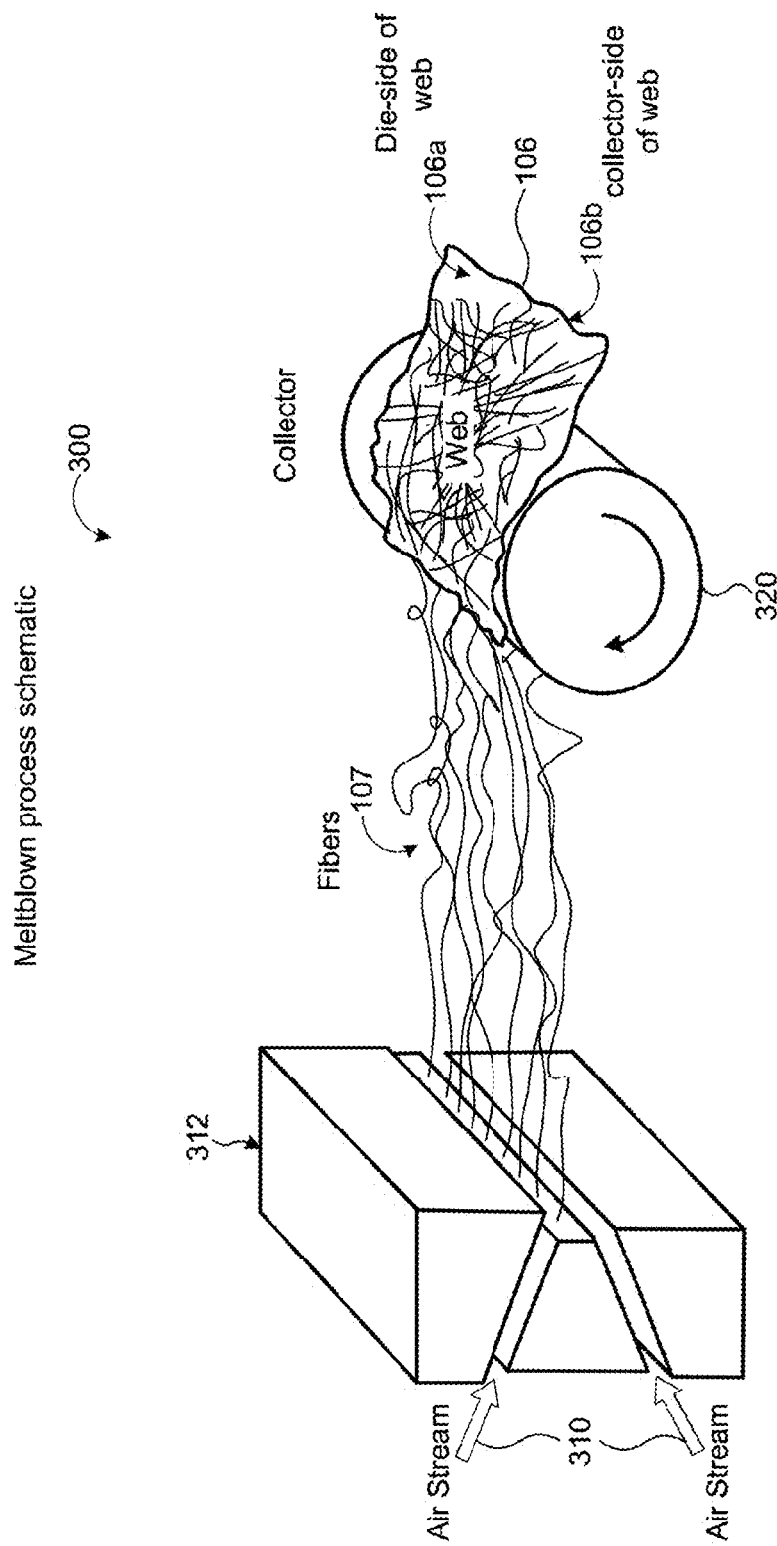
FIG. 3 is a perspective view of a device for making the abrasive meltblown layer used in the exemplary cleaning pad.

As shown in FIG. 3, the meltblown process 300 is a process that extrudes and draws molten polymer resins with a heated, high velocity air 310 to form fibers or filaments 107. The fibers/filaments 107 are cooled and are then formed into a web 106 on top of a moving screen 320. This process 300 is similar to spunbond, but the fibers 107 generated here are much finer and range in the 0.1 to 20 µm (e.g., 0.1-5 µm) diameter range. Meltblowing is also considered a spunmelt or spunlaid process. The process shown in FIG. 3 shows an extrusion die 312 (beam) that extrudes the melt blown polypropylene fibers into a continuous porous conveyor to form the nonwoven web 106. It is made up of six major components: the extruder, metering pump, extrusion die, web forming, web consolidation and winding. Other processes are possible as well.

There are two basic die designs 312 used with the meltblown technology, the single row die and the multi-row die. The key difference between these two designs is the amount of air that is used as well as the throughput of the die. With the multi-row die, much greater throughput may be achieved. Multi-row dies usually have two to eighteen rows of holes and approximately three hundred holes per inch, while the conventional single row dies have twenty-five to thirty-five holes per inch. Either die design 312 may be used to form the meltblown fibers 107. Throughput for this process is much less than the 200+ kg/hr/meter (kilograms per hour per meter) obtained for spunbond or spunlace with its much larger fiber diameters. Conventional dies basically can extrude 70 to 90 kg/hr/meter, while the multi-row die can achieve about 160 kg/hr/meter.

In some implementations, the meltblown fibers 107 have a diameter of between about 0.1 µm and about 5 µm with a mean of about 2.5 µm. Throughput and air flows have the greatest impact at reducing the fiber diameter, with melt and air temperatures and distance of the die from the forming table have less of an impact. Optimizing the process variables and using metallocene polypropylene may yield meltblown webs with mean fiber diameters in the range of 0.3 to 0.5 µm with maximum fiber diameters of less than 3 µm. A wrap layer 104 with meltblown fibers 107 of this size can provide a barrier against fluid leakage from the cleaning pad 100 by providing very high hydrohead webs with excellent breathability. The meltblown fibers 107 may be created using homopolymer polypropylene; however, several other resins can be extruded by the meltblown process as well, such as polyethylene, polyester, polyamides and polyvinyl alcohols. In some implementations, the meltblown layer 106 is formed from polylactic acids (PLA), a biodegradable nonwoven.

In some examples, the airlaid layers 101, 102, 103, the abrasion layer 104 and the wrap layer 104 (i.e., the cleaning pad 100) have a combined width WT of between about 68 millimeters and about 80 millimeters and a combined length (not shown) of between about 200 millimeters and about 212 millimeters. In some examples, the cleaning pad 100 including the airlaid layers 101, 102, 103, the abrasion layer 104 and the wrap layer 105 have a combined thickness $T_T$ of between 6.5 millimeters and about 8.5 millimeters. Additionally, or alternatively, the airlaid layers 101, 102, 103 have a combined airlaid width ($W_{A1}+W_{A2}+W_{A3}$) of between 69 millimeters and about 75 millimeters and a combined airlaid length ($L_{A1}+L_{A2}+L_{A3}$) of between about 165 millimeters and about 171 millimeters. The cleaning pad 100 withstands pressure being applied to it by an implement 400, 500 (e.g., robot or mop), since an implement 400, 500 will cause back and forth movement of the cleaning pad 100 mimicking a scrubbing action as the robot 400 traverses the floor surface 10.

In some implementations, as the cleaning pad 100 is cleaning a floor surface 10, it absorbs cleaning fluids 172 applied to the floor surface 10. The cleaning pad 100 may absorb enough fluid without changing its shape. Therefore, where the cleaning pad 100 is used along with a cleaning robot 400, the cleaning pad 100 has substantially similar dimensions before cleaning the floor surface 10 and after cleaning the floor surface 10. The cleaning pad 100 may increase in volume when it absorbs fluids. In some examples, the thickness of the cleaning pad $T_T$ increases by less than 30% after fluid absorption.

In some implementations, the wrap layer 104 has the specifications listed in Table 1 below:

TABLE 1

| Characteristic | Unit | Average Value | Tolerance | Test Method |
|---|---|---|---|---|
| Wrap Layer | | | | |
| Weight | g/m² | 55 | +/−10% | ASTM D3776M-09A |
| Thickness | mm | 0.6 | 0.55-0.65 | WSP 120.6 |
| Tensile Strength (DRY) | N/2.54 cm (MD) | 50 | >40 | ASTM D5034-09 |
| | N/2.54 cm (CD) | 25 | >20 | |
| Elongation at break (DRY) | % (MD) | 45 | 25-65 | ASTM D5034-09 |
| | % (CD) | 90 | 65-115 | |
| Water absorption | % | 600 | >500 | WSP 10.0 (05) |
| Abrasion resistance | Visual at 80 cycles | OK | No visible degradation | — |
| Meltblown Abrasive | | | | |
| Covered surface ratio | % | 50 | 44-57 | — |
| Scrubbing fiber average size | µm | N/A | 8 µm-20 µm | — |

ASTM D3776M-09A and ASTM D5034-09 are standardized tests from the American Society for Testing and Materials (ASTM). ASTM D3776M-09A covers the measurement of fabric mass per unit area (weight) and is applicable to most fabrics. ASTM D5034-09, also known as the Grab test, is a standard test method for breaking strength and elongation of textile fabrics. WSP 120.6 and WSP 10.0 (05) are standardized tests created by World Strategic Partners for testing the properties of nonwoven fabrics.

Referring to FIGS. 1A-1D, 3, 4-6 and 9A-9C, the cleaning pad 100 is configured to scrub a floor surface 10 and absorb fluids on the floor surface 10. In some examples, the cleaning pad 100 is attached to a cleaning implement such as a mobile robot 400 or a handheld mop 500. The cleaning implement 400, 500 may include a sprayer 462, 512 that sprays a cleaning fluid 172 on the floor surface 10. The implement 400, 500 is used to scrub and remove any smears (e.g., dirt, oil, food, sauces, coffee, coffee grounds) that are being absorbed by the pad 100 along with the applied fluid 172 that dissovles and/or loosens the smears 22. Some of the smears may have viscoelastic properties, which exhibit both viscous and elastic characteristic (e.g., honey). The cleaning pad 100 is absorbent and has an outer surface 105a that includes a randomly applied abrasive layer 106 comprising meltblown fibers 107. As the implement 400, 500 moves about the floor surface 10, the cleaning pad 100 wipes the floor surface 10 with the abrasive side 105b containing the abrasive layer 106b of meltblown fibers and absorbs cleaning solution sprayed onto the floor surface 10 with only a light amount of force than otherwise required by scrubbing mops having a non-abrasive cleaning element.

Figure 4:
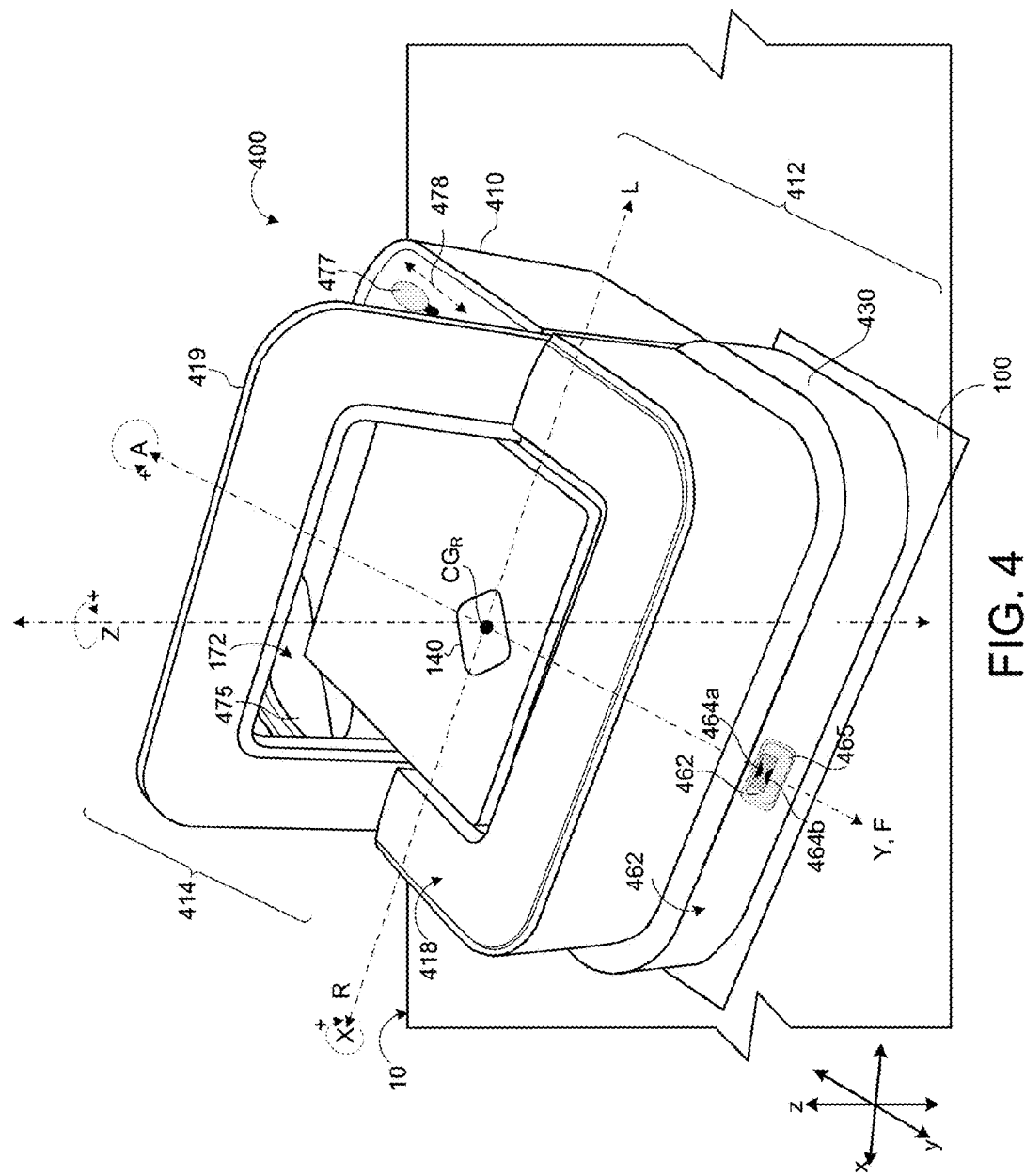
FIG. 4 is a perspective view of an autonomous mobile robot for cleaning using the exemplary cleaning pad.

Referring to FIG. 4, in some implementations, the implement 400 is a compact, lightweight autonomous mobile robot 400 that weighs less than 5 lbs and navigates and cleans a floor surface 10. The mobile robot 400 may include a body 410 supported by a drive system (not shown) that can maneuver the robot 400 across the floor surface 10 based on a drive command having x, y, and θ components, for example. As shown, the robot body 410 has a square shape. However, the body 410 may have other shapes, including but not limited to a circular shape, an oval shape, a tear drop shape, a rectangular shape, a combination of a square or rectangular front and a circular back, or a longitudinally asymmetrical combination of any of these shapes. The robot body 410 has a forward portion 412 and a rearward portion 414. The body 410 also includes a bottom portion (not shown) and a top portion 418. The bottom portion of the robot body 410 further comprises one or more rear cliff sensors (not shown) in one or both of the two rear corners of the robot 400 and one or more forward cliff sensors located in one or both of the front corners of the mobile robot 400 for preventing falls from ledged surfaces. In embodiments, the cliff sensors may be mechanical drop sensors or light based proximity sensors, such as an IR (infrared) pair, a dual emitter, single receiver or dual receiver, single emitter IR light based proximity sensor aimed downward at a floor surface 10. In some examples, the one or more forward cliff sensors and one or more rear cliff sensors are placed at an angle relative to the forward and rear corners, respectively, such that they cut the corners, spanning between sidewalls of the robot 400 and covering the corner as closely as possible to detect flooring height changes beyond a threshold accommodated by reversible robot wheel drop prior. Placing the cliff sensors proximate the corners of the robot 400 ensures that they will trigger immediately when the robot 400 overhangs a flooring drop and prevent the robot wheels from advancing over the drop edge.

In some implementations, the forward portion 412 of the body 410 carries a movable bumper 430 for detecting collisions in longitudinal (A,F) or lateral (L,R) directions. The bumper 430 has a shape complementing the robot body 410 and extends forward the robot body 410 making the overall dimension of the forward portion 412 wider than the rearward portion 414 of the robot body 410 (the robot as shown has a square shape). The bottom portion of the robot body 410 supports the cleaning pad 100. In embodiments, the pad 100 extends beyond the width of the bumper 430 such that the robot 400 can position an outer edge of the pad 100 up to and along a tough to reach surface or into a crevice, such a wall floor interface, and such that the surface or crevice is cleaned by the extended edge of the pad 100 the while the robot 400 moves in a wall following motion. The embodiment of a pad 100 extending beyond the width of the bumper 430 enables the robot 400 to clean in cracks and crevices beyond the reach of the robot body 410. In embodiments, such as those shown in FIGS. 1A-1D and FIGS. 8A-8C and 9E, the pad 100 has bluntly cut ends 100d such that the airlaid layers 101, 102, 103 are exposed at both ends 100d of the pad 100. Instead of the wrap layer 105 being sealed at the ends 100d of the pad 100 and compressing the ends 100d of the airlaid layers 101, 102, 103, the full length of the pad 100 is available for fluid absorption and cleaning. No portion of the airlaid core is compressed by the wrap layer 105 and therefore unable to absorb fluid 172. Additionally, a used disposable pad 100 of this embodiment will not have soaking wet, floppy ends of sealed wrap layer 105 at the completion of a cleaning run. All fluid 172 will be securely absorbed and held by the airlaid core, preventing any drips and preventing a user from undesirably contacting dirty wet ends of the pad 100.

As shown in FIGS. 4 and 9A-9G, the robot 400 may drive back and forth to cover a specific portion of the floor surface 10. As the robot 400 drives back and forth, it cleans the area it is traversing and therefore provides a deep scrub to the floor surface 10. A reservoir 475 housed by the robot body 410 holds a cleaning fluid 172 (i.e. cleaning solution) and may hold 170-230 mL of fluid. In embodiments, the reservoir 475 holds 200 mL of fluid. The robot 400 may include a fluid applicator 462 connected to the reservoir 475 by a tube. The fluid applicator 462 may be a sprayer having at least one nozzle 464 that distributes fluid over the floor surface 10. The fluid applicator 462 may have multiple nozzles 464 each configured to spray the fluid at an angle and distance different than another nozzle 464. In some examples, the robot 400 includes two nozzles 464, vertically stacked in a recess in the fluid applicator 462 and angled and spaced such that one nozzle 464a sprays relatively longer lengths of fluid 172a forward and downward to cover an area in front of the robot 400 with a a forward supply of applied fluid 173a and the other nozzle 464b sprays relatively shorter lengths fluid 172b forward and downward to leave a rearward supply of applied fluid 173b on an area in front of but closer to the robot 400 than the area of applied fluid 173a dispensed by the top nozzle 464a. In embodiments, the nozzle 464 or nozzles 464a, 464b dispense fluid 172, 172a, 172b in an area pattern that extends one robot width $W_R$ and at least one robot length $L_R$ in dimension. In some embodiments, the top nozzle 464a and bottom nozzle 464b apply fluid 172a, 172b in two distinct spaced apart strips of applied fluid 173a, 173b that do not extend to the full width $W_R$ of the robot 400 such that the pad 100 passes through the outer edges of the strips of applied fluid 173a, 173b in forward and backward angled scrubbing motions as described herein. In embodiments, the strips of applied fluid 173a, 173b cover a width $W_S$ of 75-95% of the robot width $W_R$ and a combined length $L_S$ of 75-95% of the robot length $L_R$. In some implementations, the robot 400 only sprays on traversed areas of the floor surface 10.

Moreover, the back and forth movement of the robot 400 breaks down stains on the surface floor 10. The broken down stains are then absorbed by the cleaning pad 100. In some examples, the cleaning pad 100 picks up enough of the sprayed fluid to avoid uneven streaks if the cleaning pad 100 picks up too much liquid, e.g fluid 172. In case of too little fluid absorption, the robot 400 might leave fluid and wheel traces. In some embodiments, the cleaning pad 100 leaves a residue of the fluid, which could be water or some other cleaning agent including solutions containing cleansing agents, to provide a visible sheen on the surface floor 10 being scrubbed. In some examples, the fluid contains antibacterial solution, e.g., an alcohol containing solution. A thin layer of residue, therefore, is purposely not absorbed by the cleaning pad 100 to allow the fluid to kill a higher percentage of germs. Therefore, the cleaning pad 100 does not swell or expand and provides a minimal increase in total pad thickness $T_T$. This characteristic of the cleaning pad 100 prevents the robot 400 from tilting backwards or pitching up if the cleaning pad 100 expands. The cleaning pad 100 is sufficiently rigid to support the front of the robot. In some examples, the cleaning pad 100 absorbs up to 180 ml or 90% of the total fluid contained in the robot reservoir 475. In some examples, the cleaning pad holds about 55 to about 60 ml of fluid and a fully saturated wrap layer holds about 6 to about 8 ml of fluid 172. In some examples the ratio of fluid retention in the airlaid core 101,102,103 to the outer wrap layer 105 is about 9:1 to about 5:1.

The pad 100 and robot 400 are sized and shaped such that the transfer of fluid from the reservoir to the absorptive pad 100 maintains the forward and aft balance of the less than 5 lb robot 400 during dynamic motion. The fluid distribution is designed so that the robot 400 continually propels the pad 100 over a floor surface 10 without the interference of the increasingly saturated pad 100 and decreasingly occupied fluid reservoir 475 lifting the back 414 of the robot 400 and pitching the front 412 of the robot 400 downward and thereby applying movement-prohibitive downward force to the robot 400. The robot 400 is able to move the pad 100 across the floor surface 10 even when the pad 100 is fully saturated with fluid. The robot 400 however includes the feature of tracking the amount of floor surface 10 travelled and/or the amount of fluid remaining in the reservoir 475 and provides an audible and/or visible alert to a user that the pad 100 requires replacement and/or the reservoir 475 requires refilling. In embodiments, the robot 400 stops moving and remains in place on the floor surface if the pad 100 is fully saturated, and there remains floor to be cleaned once the pad 100 is replaced.

FIGS. 9A through 9G detail the spraying, pad wetting, and scrubbing motions of one embodiment of the mobile robot 400. In some implementations, the robot 400 only applies fluid 172 to areas of the floor surface 10 that the robot 100 has already traversed. In one example, the fluid applicator 462 has multiple nozzles 464a, 464b each configured to spray the fluid 172a, 172b in a direction different than another nozzle 464a, 164b. The fluid applicator 462 may apply fluid 172 downward rather than outward, dripping or spraying fluid 172 directly in front of the robot 100. In some examples, the fluid applicator 462 is a microfiber cloth or strip, a fluid dispersion brush, or a sprayer.

Figure 9A:
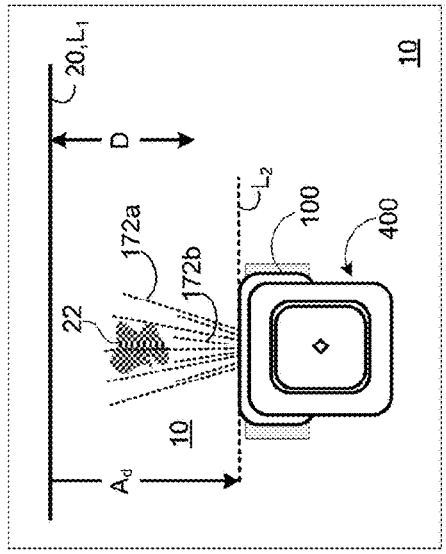
FIGS. 9A-9C are top views of an exemplary autonomous mobile robot as it sprays a floor surface with a fluid.
Figure 9B:
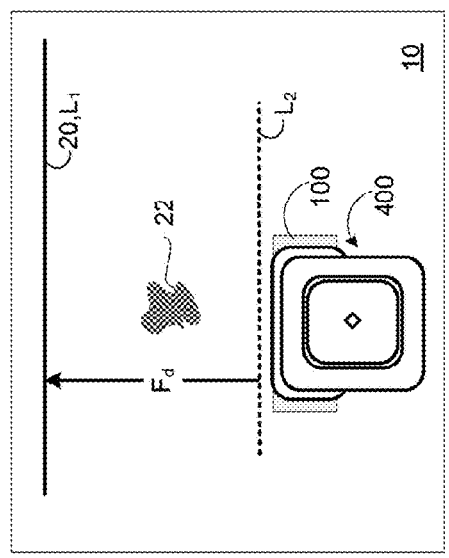

Referring to FIGS. 9A-9D and 9F-9G, in some implementations, the robot 400 may execute a cleaning behavior by moving in a forward direction F toward an obstacle 20, followed by moving in a backward or reverse direction A. As indicated in FIGS. 9A and 9B, the robot 400 may drive in a forward drive direction a first distance Fd to a first location L1. As the robot 400 moves backwards a second distance Ad to a second location L2, the nozzles 464a, 464b simultaneously spray longer lengths fluid 172a and shorter lengths of fluid 172b onto the floor surface 10 in a forward and/or downward direction in front of the robot 400 after the robot 400 has moved at least a distance D across an area of the floor surface 10 that was already traversed in the forward drive direction F. In one example, the fluid 172 is applied to an area substantially equal to or less than the area footprint AF of the robot 400. Because distance D is the distance spanning at least the length $L_R$ of the robot 400, the robot 400 determines that the area of floor 10 traverses is clear floor surface 10 unoccupied by furniture, walls 20, cliffs, carpets or other surfaces or obstacles onto which cleaning fluid 172 would be applied if the robot 100 had not already verified the presence of a clear floor surface 10 for receiving cleaning fluid 172. By moving in a forward direction F and then backing up prior to applying cleaning fluid 172, the robot 400 identifies boundaries, such as a flooring changes and walls, and prevents fluid damage to those items.

Figure 9C:
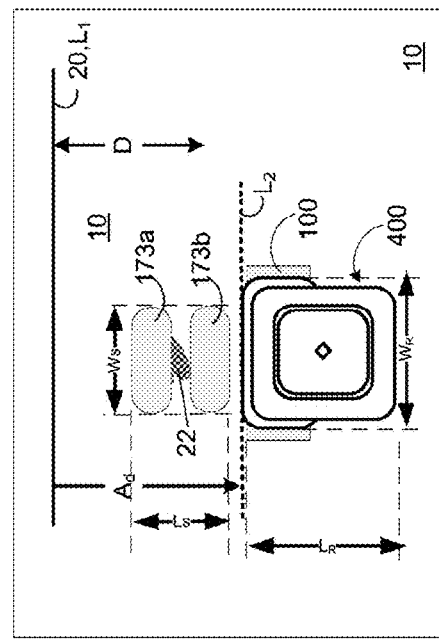

As shown in FIGS. 4, 9B and 9C, in some examples, the fluid applicator 462 is a sprayer 462 that includes at least two nozzles 464a, 464b, each distributing the fluid 172 evenly across the floor surface 10 in two strips of applied fluid 173a, 173b. The two nozzles 464a, 464b are each configured to spray the fluid at an angle and distance different than another nozzle 464a, 464b. In some examples, the two nozzles 464a, 464b are vertically stacked in a recess in the fluid applicator 462 and angled from horizontal and spaced apart from one another such that one nozzle 464a sprays relatively longer lengths of fluid 172a forward and downward to cover an area in front of the robot 400 with a forward supply of applied fluid 173a, and the other nozzle 464b sprays relatively shorter lengths fluid 172b forward and downward to leave a rearward supply of applied fluid 173b on an area in front of but closer to the robot 400 than the area of applied fluid 173a dispensed by the top nozzle 464a. In embodiments, the nozzle 464 or nozzles 464a, 464b dispense fluid 172, 172a, 172b in an area pattern that extends one robot width $W_R$ and at least one robot length $L_R$ in dimension. In some embodiments, the top nozzle 464a and bottom nozzle 464b apply fluid 172a, 172b in two distinct spaced apart strips of applied fluid 173a, 173b that do not extend to the full width $W_R$ of the robot 400 such that the pad 100 passes through the outer edges of the strips of applied fluid 173a, 173b in forward and backward angled scrubbing motions as described herein. In embodiments, the strips of applied fluid 173a, 173b cover a width $W_S$ of 75-95% of the robot width $W_R$ and a combined length $L_S$ of 75-95% of the robot length $L_R$. In embodiments, the strips of applied fluid 173a, 173b may be substantially rectangular shaped or ellipse shaped. In embodiments, the nozzles 464a, 464b complete each spray cycle by sucking in a small volume of fluid at the opening of the nozzle so that no fluid 172 leaks from the nozzle following each instance of spraying.

Figure 9D:
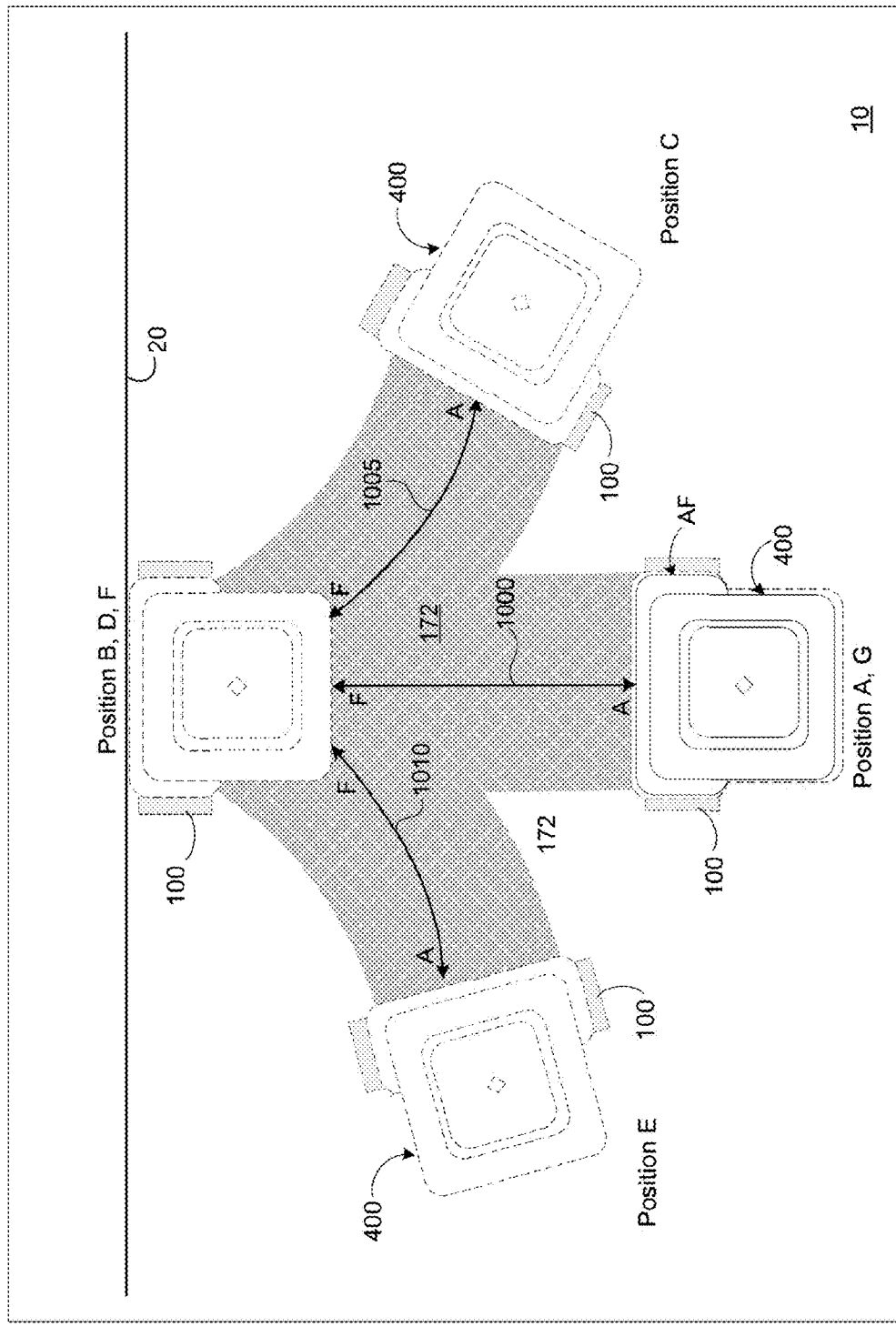
FIG. 9D is a top view of an exemplary autonomous mobile robot as it scrubs a floor surface.
Figure 9E:
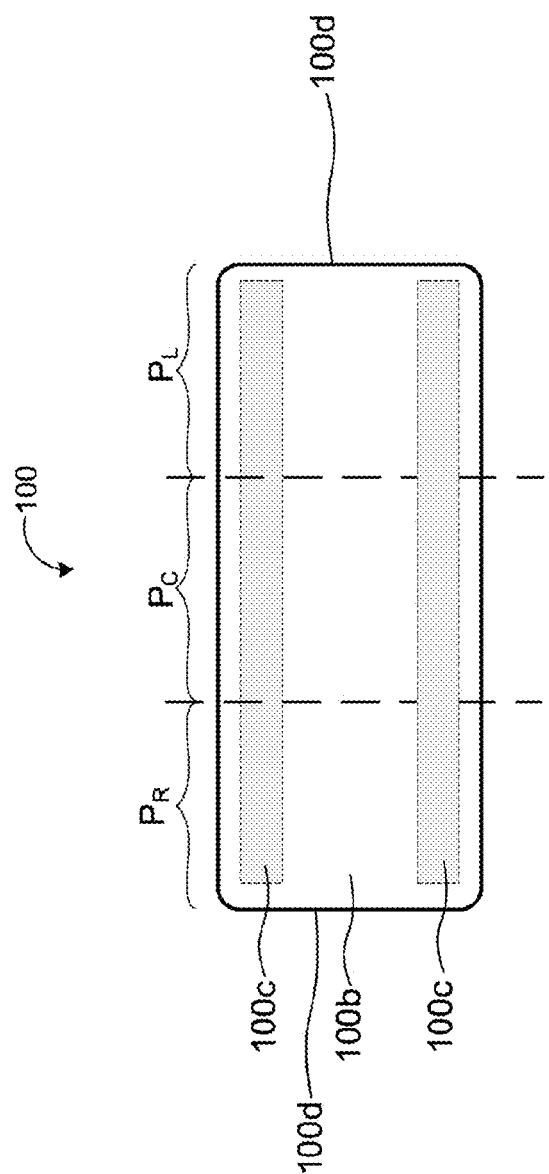
FIG. 9E is a bottom view of an exemplary cleaning pad.
Figure 9F:
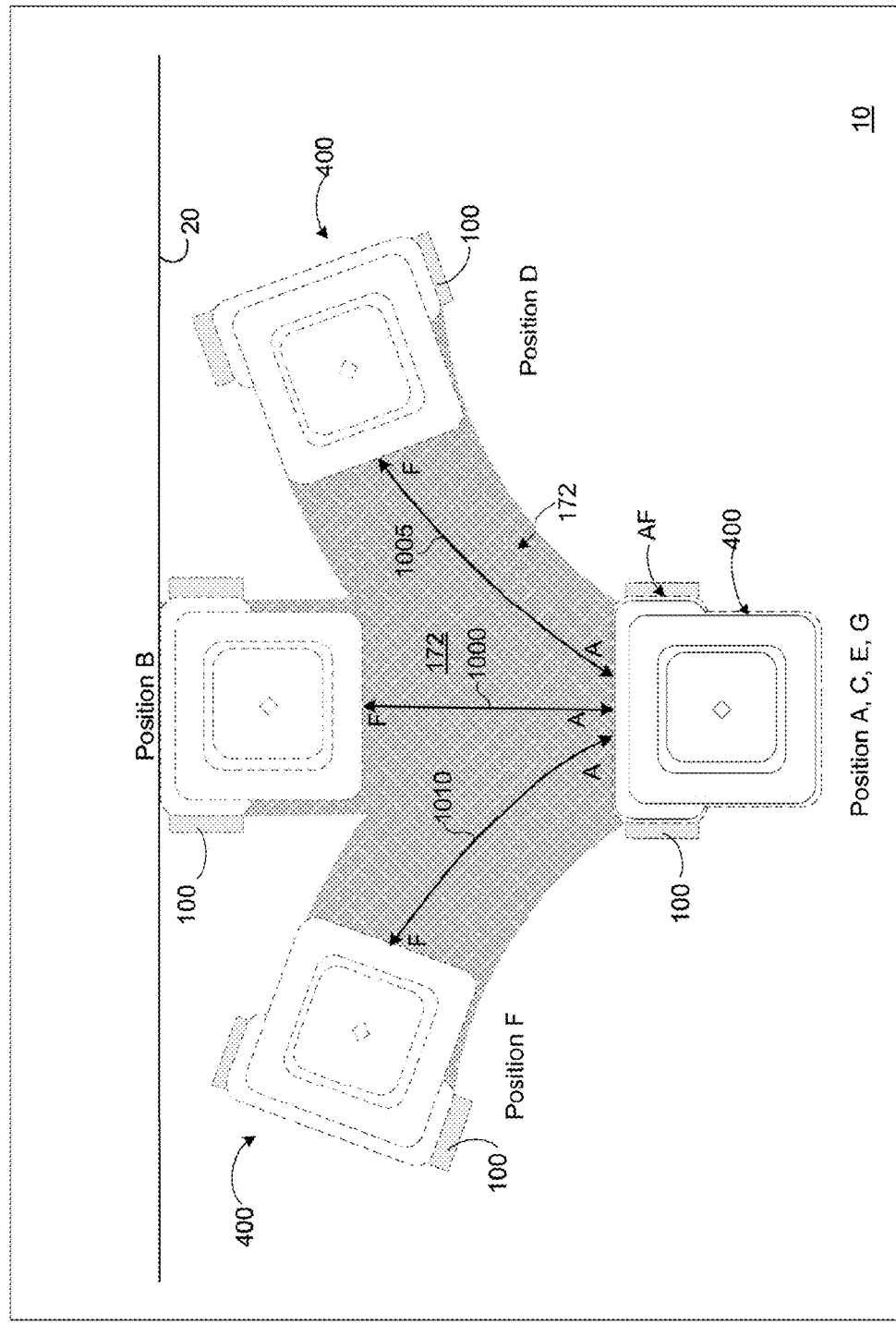
FIG. 9F is a top view of an exemplary autonomous mobile robot as it scrubs a floor surface.
Figure 9G:
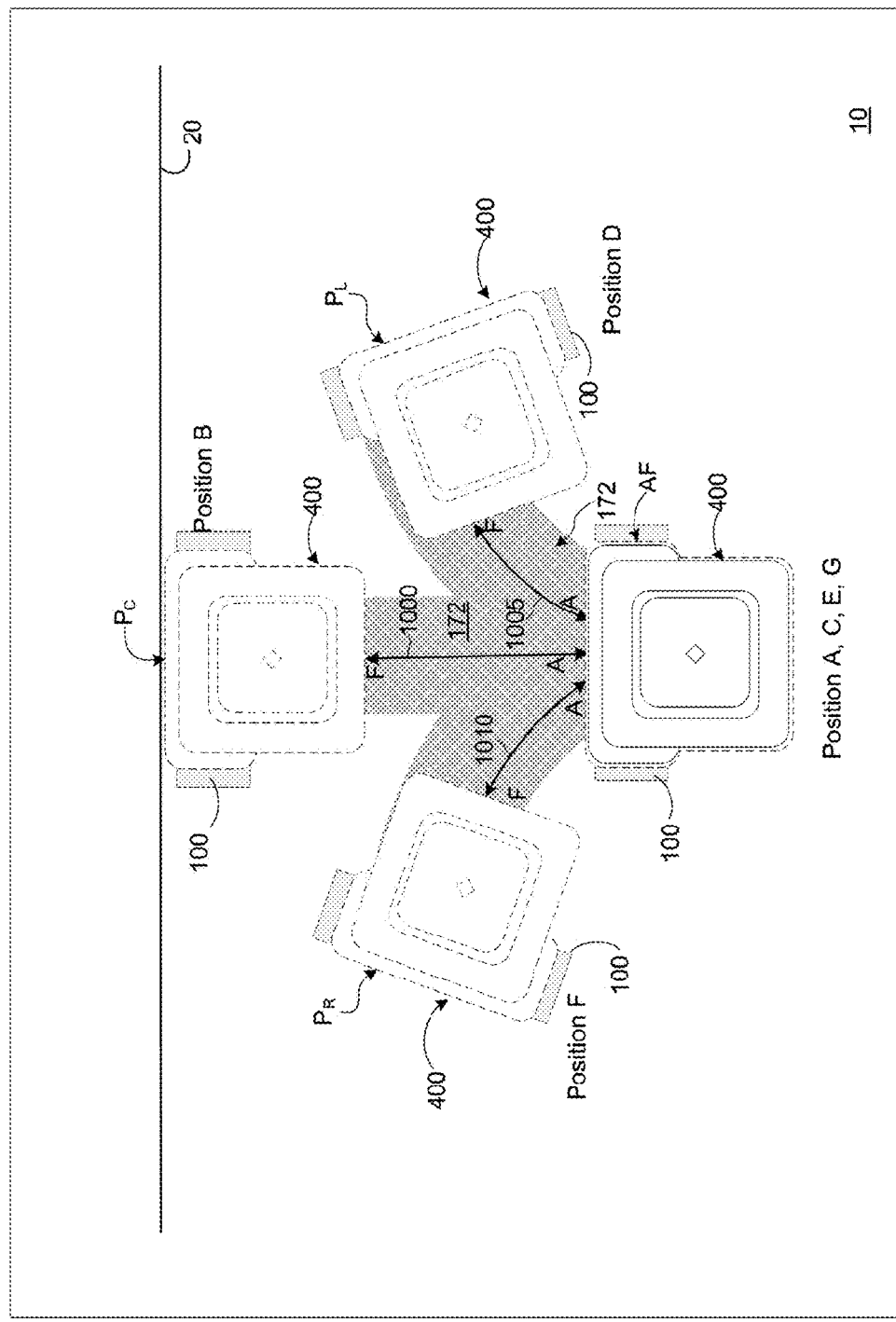
FIG. 9G is a top view of an exemplary autonomous mobile robot as it scrubs a floor surface.

Referring to FIGS. 9D, 9F and 9G, in some examples, the robot 400 may drive back and forth to cover a specific portion of the floor surface 10, wetting the cleaning pad 100 at the start of a cleaning run and/or scrubbing the floor surface 10. The robot 400 drives back and forth, cleaning the area traverse and therefore providing a thorough scrub to the floor surface 10. The robot 400 oscillates the attached pad 100 in an orbit of 12-15 mm to scrub the floor 10 and applies 1 pound of downward pushing force or less to the pad.

Figure 10:
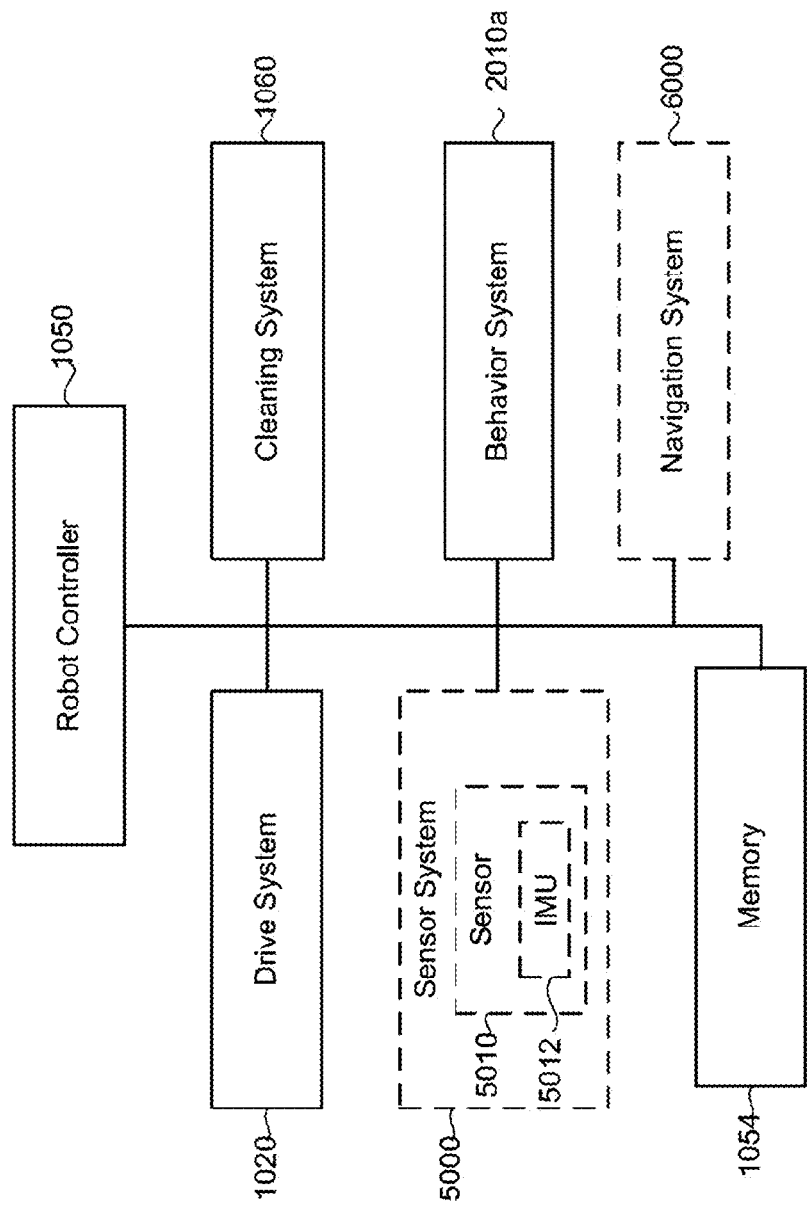
FIG. 10 is a schematic view of the robot controller of the exemplary autonomous mobile robot of FIG. 4.

In some examples, the fluid applicator 462 applies fluid 172 to an area in front of the cleaning pad 100 and in the direction of travel (e.g., forward direction F) of the mobile robot 100. In some examples, the fluid 172 is applied to an area the cleaning pad 100 has previously occupied. In some examples, the area the cleaning pad 100 has occupied is recorded on a stored map that is accessible to a robot controller 150, as shown in the diagram of FIG. 10. The robot 400 may include a cleaning system 1060 for cleaning or treating a floor surface 10.

In some examples, the robot 400 knows where it has been based on storing its coverage locations on a map stored on the non-transitory-memory 1054 of the robot 400 or on an external storage medium accessible by the robot 400 through wired or wireless means during a cleaning run. The robot 400 sensors 5010 may include a camera and/or one or more ranging lasers for building a map of a space. In some examples, the robot controller 1050 uses the map of walls, furniture, flooring changes and other obstacles 10 to position and pose the robot 400 at locations far enough away from obstacles and/or flooring changes prior to the application of cleaning fluid 172. This has the advantage of applying fluid 172 to areas of floor surface 10 having no known obstacles thereon.

In some examples, the robot 100 moves in a back and forth motion to moisten the cleaning pad 100 and/or scrub the floor surface 10 to which fluid 172 has been applied. The robot 400 may move in a birdsfoot pattern through the footprint area AF on the floor surface 10 to which fluid 172 has been applied. As depicted, in some implementations, the birdsfoot cleaning routine involves moving the robot 100 in forward direction F and a backward or reverse direction A along a center trajectory 1000 and in forward direction F and a backward direction A along left 1010 and right 1005 trajectories. In some examples, the left trajectory 1010 and the right trajectory 1005 are arcuate trajectories that extend outward in an arc from a starting point along the center trajectory 1000. The left trajectory 1010 and the right trajectory 1005 may be straight line trajectories that extend outward in a straight line from the center trajectory 1000.

FIGS. 9D and 9F depict two birdsfoot trajectories. In the example of FIG. 9D, the robot 400 moves in a forward direction F from Position A along the center trajectory 1000 until it encounters a wall 20 and triggers a sensor 5010, such as a bump sensor, at Position B. The robot 400 then moves in a backward direction A along the center trajectory to a distance equal to or greater than the distance to be covered by fluid application. For example, the robot 400 moves backward along the center trajectory 1000 by at least one robot length l to Position G, which may be the same position as Position A. The robot 400 applies fluid 172 to an area substantially equal to or less than the footprint area AF of the robot 100 and returns to the wall 20, the cleaning pad 400 passing through the fluid 172 and cleaning the floor surface 10. From position B, the robot 100 retracts either along a left trajectory 1010 or a right trajectory 1005 before returning to Position B and covering the remaining trajectory. Each time the robot 400 moves forward and backward along the center trajectory 1000, left trajectory 1010 and right trajectory 1005, the cleaning pad 100 passes through the applied fluid 172, scrubbing dirt, debris and other particulate matter from the floor surface 10 to which the fluid 172 is applied and absorbing the dirty fluid into the cleaning pad 100 and away from the floor surface 10. The scrubbing motion of the moistened pad combined with the solvent characteristics of the cleaning fluid 172 breaks down and loosens dried stains and dirt. The cleaning fluid 172 applied by the robot 400 suspends loosened debris such that the cleaning pad 100 absorbs the suspended debris and wicks it away from the floor surface 10.

In the example of FIG. 9F, the robot 400 similarly moves from a starting position, Position A, through applied fluid 172, along a center trajectory 1000 to a wall position, Position B. The robot 400 backs off of the wall 20 along the center trajectory 1000 to Position C, which may be the same position as Position A, before covering left and right trajectories 1010, 1005, extending to positions D and F, with the cleaning fluid 172 distributed along the trajectories 1010, 1005 by the cleaning pad 100. In one example, each time the robot 400 extends along a trajectory outward from the center trajectory 1000, the robot 400 returns to a position along the center trajectory as indicated by Positions A, C, E and G, as depicted in FIG. 9F. In some implementations, the robot 400 may vary the sequence of backward direction A movements and forward direction F movements along one or more distinct trajectories to move the cleaning pad 100 and cleaning fluid 172 in an effective and efficient coverage pattern across the floor surface.

In some examples, the robot 100 may move in a birdsfoot coverage pattern to moisten all portions of the cleaning pad 100 upon starting a cleaning run. As depicted in FIG. 9E, the bottom surface 100b of the cleaning pad 100 has a center area PC and right and left lateral edge areas PR and PL. When the robot 100 starts a cleaning run, or cleaning routine, the cleaning pad 100 is dry and needs to be moistened to reduce friction and also to spread cleaning fluid 172 along the floor surface 10 to scrub debris therefrom.

The robot 400 therefore applies fluid at a higher volumetric flow rate initially at the start of a cleaning run such that the cleaning pad 100 is readily moistened. In one implementation, the first volumetric flow rate is set by spraying about 1 mL of fluid every 1.5 feet initially for a period of time such as 1-3 minutes, and the second volumetric flow rate is set by spraying every 3 feet, wherein each spray of fluid is less than 1 mL of volume. In embodiments, the robot 400 applies fluid 172 every one to two feet at the start of a run to saturate the wrap layer 105 of the pad 100 early in the cleaning run. After a period of time and/or distance, such as a duration of 2-10 minutes, the robot 400 applies fluid at intervals of every three to five feet because the pad 100 is moistened and able to scrub the floor 10. As FIG. 9G depicts, in some examples, at the start of a cleaning run, the robot 400 drives the cleaning pad 100 through applied fluid 172 such that the center area PC of the bottom surface 100b of the cleaning pad 100 and the left and right lateral edge areas PR and PL of the cleaning pad 100 each pass through the applied fluid 172 separately, thereby moistening the entire cleaning pad 100 along the entire bottom surface 100b of the cleaning pad 100 in contact with the floor surface 10.

In the example of FIG. 9G, the robot 400 moves in a forward direction F and 10 then backward direction A along a center trajectory 1000, passing the center of the pad 100 through the applied fluid 172. The robot 400 then drives in a forward direction F and backward direction A along a right trajectory 1005, passing the left lateral area PL of the cleaning pad 100 through the applied fluid 172. The robot 100 then drives in a forward direction F and backward direction A along a left trajectory 1010, passing the right lateral area PR of the cleaning pad 100 through the applied fluid 172. At the start of the cleaning run, the robot applies fluid 172 at a relatively high initial volumetric flow rate Vi and/or high initial frequency of application, applying a larger quantity of fluid 172 more frequently to the surface 10 and/or applying a fixed amount of fluid 172 more frequently to the surface 10 to moisten the cleaning pad 100 quickly. Moistening the cleaning pad reduces friction and also enables the pad 100 to dissolve more debris 22 without requiring more frequent applications of fluid 172. In embodiments, the coefficient of friction of the warp layer 105 of the pad 100 varies from 0.3 to 0.5 depending on material of the floor 10 and wetness of the pad 100. In one embodiment, a dry pad 100 moving on glass has a coefficient of friction of around 0.4 to 0.5, and wet on tiles has a coefficient of friction of about 0.25 to 0.4.

Once the wrap layer 105 of the cleaning pad 100 is moistened, the robot 400 continues its cleaning run and subsequently applies fluid 172 at a second volumetric flow rate Vf. This second volumetric flow rate Vf is relatively lower than the initial flow rate Vi at the start of the cleaning run because the cleaning pad 100 is already moistened and effectively moves cleaning fluid across the surface 10 as it scrubs. In one implementation, the initial volumetric flow rate Vi is set by spraying about 1 mL of fluid every 1.5 feet initially for a period of time such as 1-3 minutes, and the second volumetric flow rate Vf is set by spraying every 3 feet, wherein each spray of fluid is less than 1 mL of volume. The robot 400 adjusts the volumetric flow rate V such that a cleaning pad 100 of specified dimensions is moistened on the bottom surface 100b (FIG. 9E) without being fully wetted to capacity internally in the airlaid layers 101, 102, 103. The bottom surface 100b of the cleaning pad 100 is initially moistened without the absorbent interior of the pad 100 being water logged such that the cleaning pad 100 remains fully absorbent for the remainder of the cleaning run. The back and forth movement of the robot 400 breaks down stains 22 on the floor surface 10. The broken down stains 22 are then absorbed by the cleaning pad 100.

In some examples, the cleaning pad 100 picks up enough of the sprayed fluid 172 to avoid uneven streaks. In some examples, the cleaning pad 100 leaves a residue of the solution to provide a visible sheen to the floor surface 10 being scrubbed. In some examples, the fluid 172 contains antibacterial solution; therefore, a thin layer of residue is purposely not absorbed by the cleaning pad 100 to allow the fluid 172 to kill a higher percentage of germs.

In an embodiment, the pad may be scented. The scent agent may be integrated into or applied onto one or more of the airlaid core layers, the liner or a combination of the airlaid layers and liner. The scenting agent may be inert in a pre-activation stage and activated by fluid to release scent so that the pad only produces a scent during use and otherwise produces no scent while stored. In another embodiment, the pad includes a cleaning agent or surfactant that may be integrated into or applied onto one or more of the airlaid core layers, the liner, or a combination of the airlaid layers and liner. In one embodiment, the cleaning agent is applied to only the back surface (unexposed, non-meltblown side) of the liner in contact with the lower most airlaid core member such that the cleaning agent is released through the porous liner, onto the cleaning surface when in contact with fluid. The cleaning agent may be a foaming agent and/or a cleaning agent with a visibly glossy sheen indicating the application of the cleaning agent the cleaning surface. In another embodiment, the pad includes one or more chemical preservatives applied to or manufactured within the cardboard backing element. The preservatives are selected to prevent the growth of wood spores that may be present in the wood based backing element. Some embodiments of the pad may include all of these features—conventional scent agent, cleaning agent, antibacterial agent and preservatives—or combinations of fewer than all of these features, including, for example, an encapsulated scent.

Figure 5:
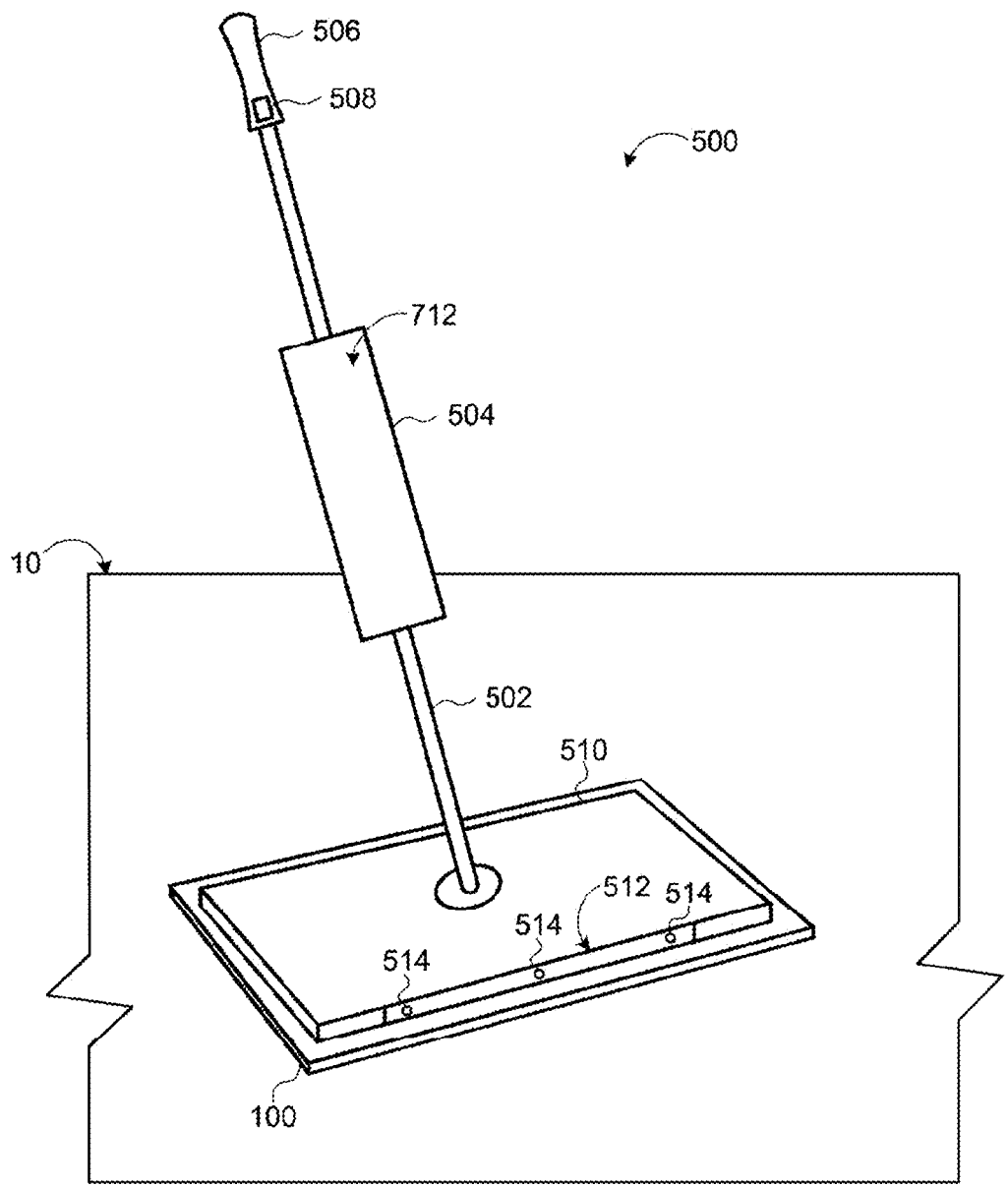
FIG. 5 is a perspective view of a mop using the exemplary cleaning pad.
Figure 6:
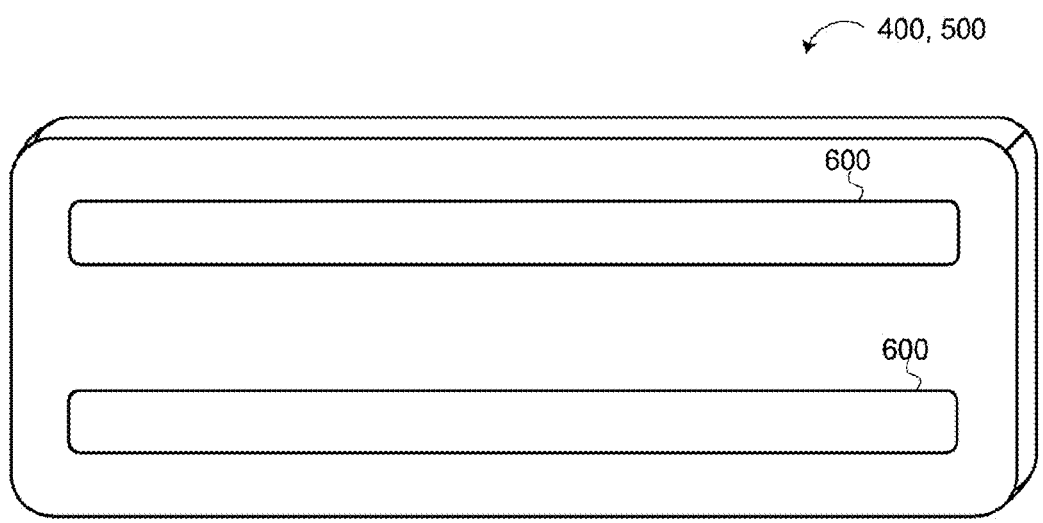
FIG. 6 is a bottom view of an exemplary cleaning pad.

Referring to FIG. 5, in some examples, the implement 500 is a mop 500. The mop 500 includes a body 502 supporting a reservoir 504 that holds a cleaning fluid 172 (e.g. a cleaning solution). A handle 506 is disposed on one side of the body 502. The handle includes a controller 508 for controlling the release of the fluid from the reservoir 504. A movable rotatable base 510 is disposed on the other end of the body 502 opposite the handle 506. The base 510 includes a fluid applicator 512 connected to the reservoir 504 by a tube (not shown). The fluid applicator 512 may be a sprayer having at least one nozzle 514 that distributes fluid over the floor surface 10. The nozzle 514 sprays forward and downwards of the base 510 towards the floor surface 10. A user controlling the controller 508 sprays the fluid 172 when needed. The fluid applicator 512 may have multiple nozzles 514 each configured to spray the fluid in a direction different than another nozzle 514.

Referring to FIGS. 6, and 8E-8G, a retainer 600, 600a, 600b may be disposed on the implement 400, 500 supporting the cleaning pad 100. The retainer 600, 600a, 600b is disposed on a bottom portion of the implement 400, 500 for retaining the cleaning pad 100. In one embodiment, the retainer 600 may include hook-and-loop fasteners, and in another embodiment, the retainer 600 may include clips, or retention brackets, and selectively moveable clips or retention brackets for selectively releasing the pad for removal. Other types of retainers may be used to connect the cleaning pad 100 to implement 400, 500, such as snaps, clamps, brackets, adhesive, etc., which may be configured to allow the release of the cleaning pad 100 upon activation of a pad release mechanism located on the implement 400, 500 such that user need not touch the dirty used pad to remove the pad from the cleaning implement 400, 500.

Figure 7:
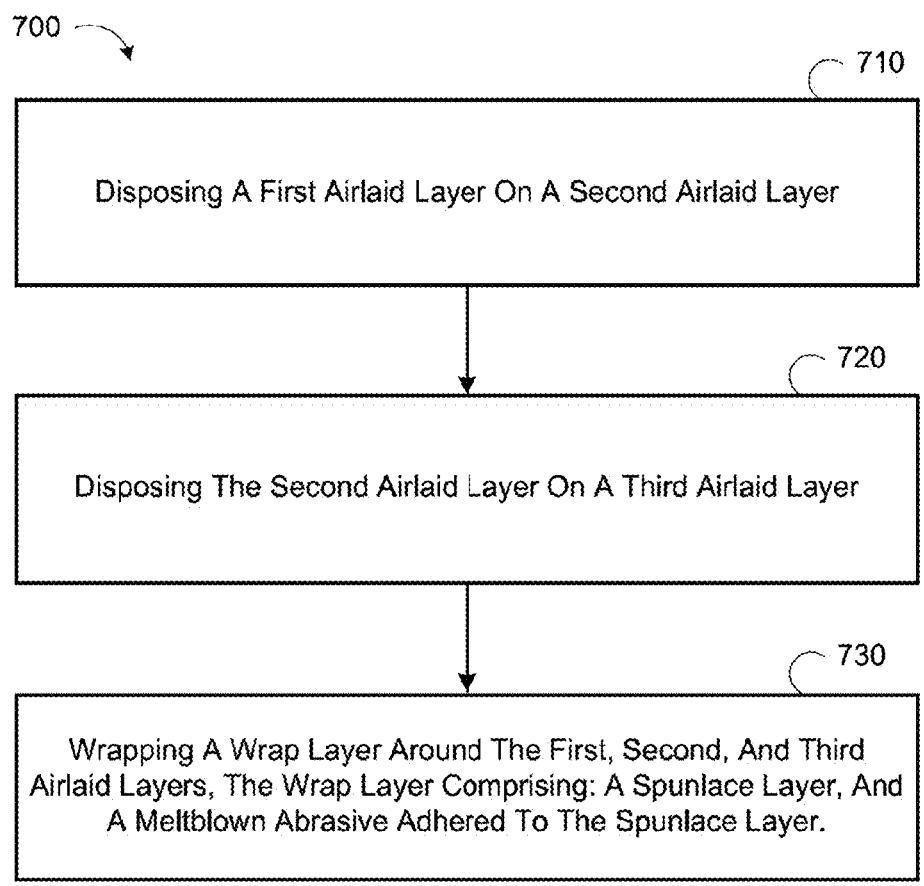
FIG. 7 is a schematic view of an exemplary arrangement of operations for constructing a cleaning pad.

FIG. 7 provides an exemplary arrangement of operations for a method 700 of constructing a cleaning pad 100. The method 700 includes disposing 710 a first airlaid layer 101 on a second airlaid layer 102 and disposing 720 the second airlaid layer 102 on a third airlaid layer 103. The method 700 further includes wrapping 730 a wrap layer 104 around the first, second, and third airlaid layers 101, 102, 103. The wrap layer 104 includes a spunlace wrap layer 105, and a meltblown abrasive 107 adhered to the spunlace wrap layer 105.

In some examples, the method 700 further includes adhering and randomly arranging meltblown abrasive 107 on the spunlace wrap layer 105. Additionally or alternatively, the meltblown abrasive fibers may have a diameter of between about 0.1 µm and about 20 µm. The method 700 may further include arranging the meltblown abrasive and the spunlace wrap layer 105 to have a collective thickness of between 0.5 mm and about 0.7 mm on the spunlace wrap layer 105. In some examples, the meltblown abrasive 107 creates a thickness gap of 0.5 mm between the wrap layer 105 and the floor 10. Because of this thickness gap, the pad 100 can pick up a 1.5 mm diameter bubble of fluid sitting on the floor 10 with surface tension without requiring force. The lowest points of the embossed cover 105 layer are only 0.5 mm from the floor 10 and the remainder of the surface area of wrap layer 105 is 3 mm from the floor 10.

The method 700 may further include arranging the meltblown abrasive 107 on the spunlace wrap layer 105 to provide a covered surface ratio between the meltblown abrasive 107 and the spunlace wrap layer 105 of between about 60% and about 70%. In some examples, the method 700 may include adhering the first airlaid layer 101 to the second airlaid layer 102 and adhering the second airlaid layer 102 to the third airlaid layer 103. The airlaid layers 101, 102, 103 may be of a cellulose based textile material (e.g., a material including fluff pulp).

In some implementations, the method 700 may include where the first, second, and third airlaid layers 101, 102, 103, the spunlace wrap layer 105, and the meltblown abrasive are configured to increase in thickness by less than 30% after fluid absorption. The method 700 may further include embossing the spunlace layer 105. The method 700 may also include disposing sodium polyacrylate in one or more of the airlaid layers 101, 102, 103.

In some examples, the method 700 further includes configuring the airlaid layers 101, 102, 103 and wrap layer 104 to have a combined width of between about 80 millimeters and about 68 millimeters, and a combined length of between about 200 millimeters and about 212 millimeters. The method 700 may further include configuring the airlaid layers 101, 102, 103 and the wrap layer 104 to have a combined thickness of between about 6.5 millimeters and about 8.5 millimeters. The method 700 may include configuring the airlaid layers 101, 102, 103 to have a combined airlaid width of between 69 millimeters and about 75 millimeters, and a combined airlaid length of between about 165 millimeters and about 171 millimeters.

Figure 8E:
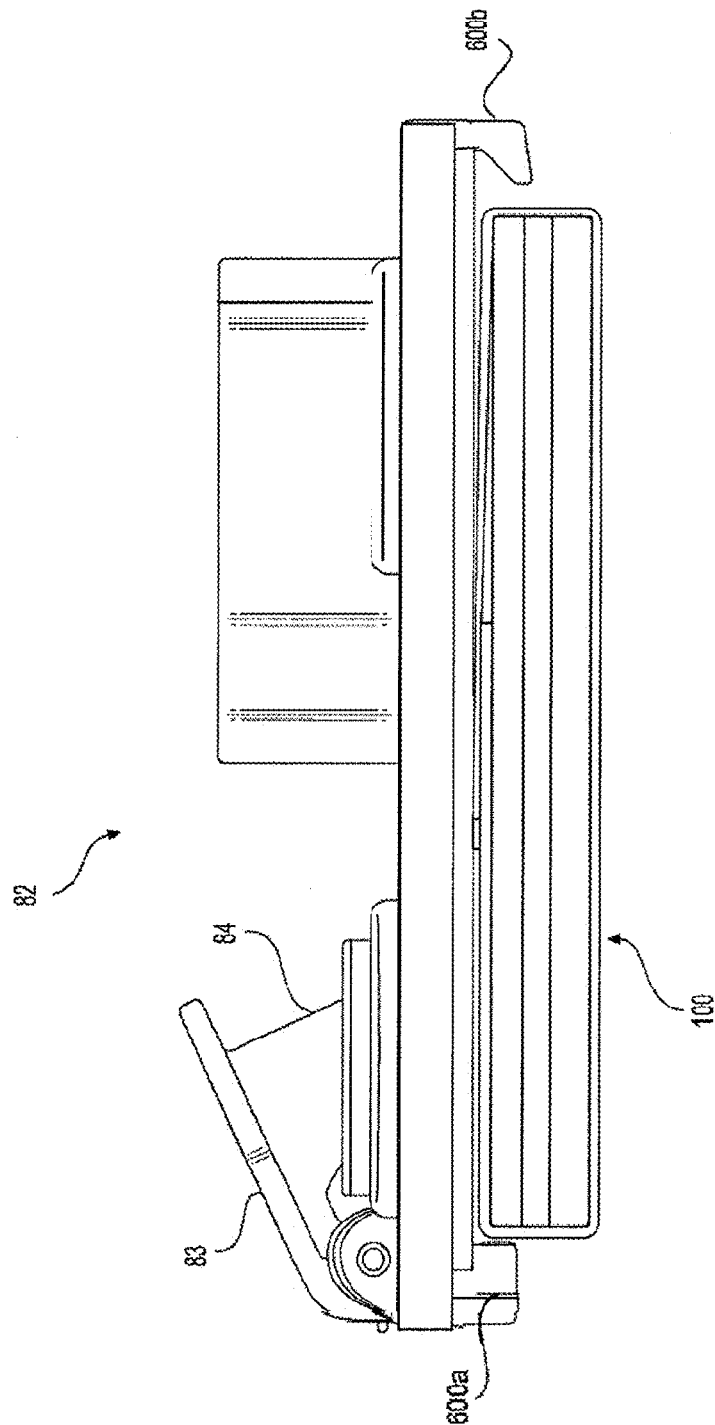
FIG. 8E is a side view of an exemplary attachment mechanism for a pad as described herein in a secure position.
Figure 8F:
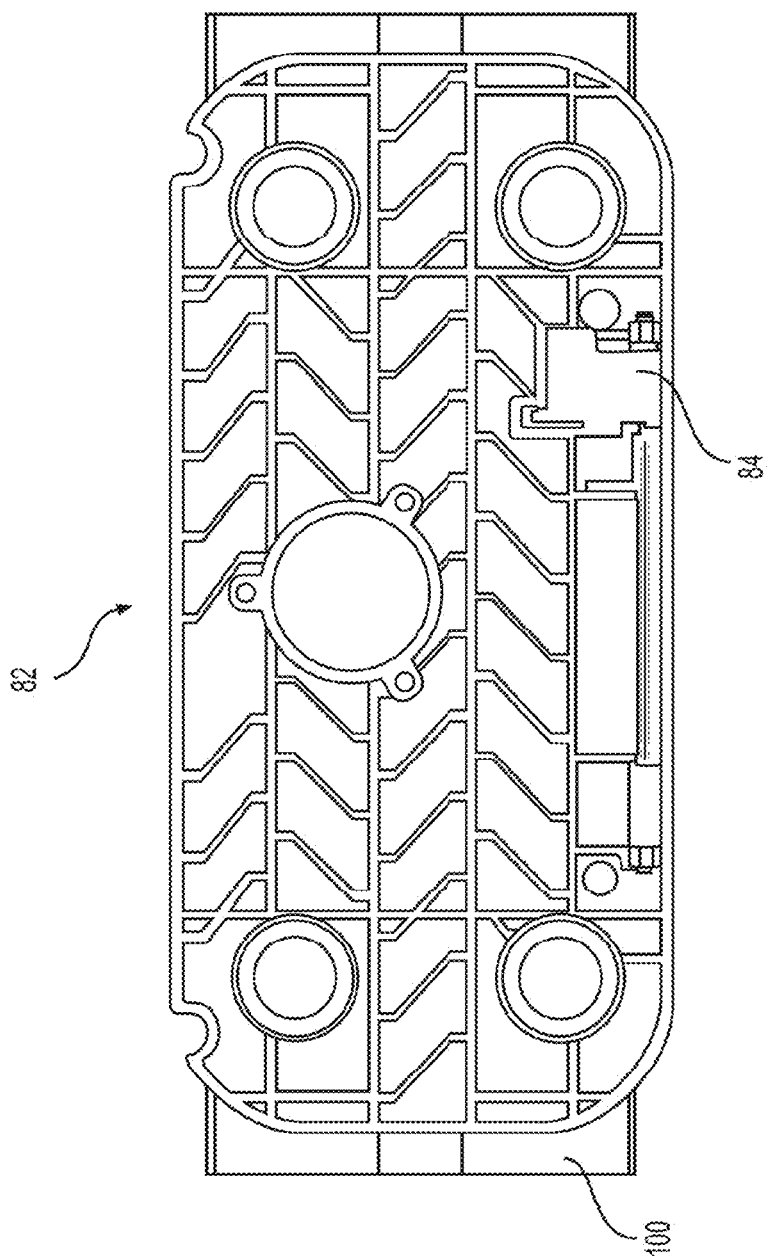
FIG. 8F is a top view of an exemplary attachment holder for the pad as described herein.
Figure 8G:
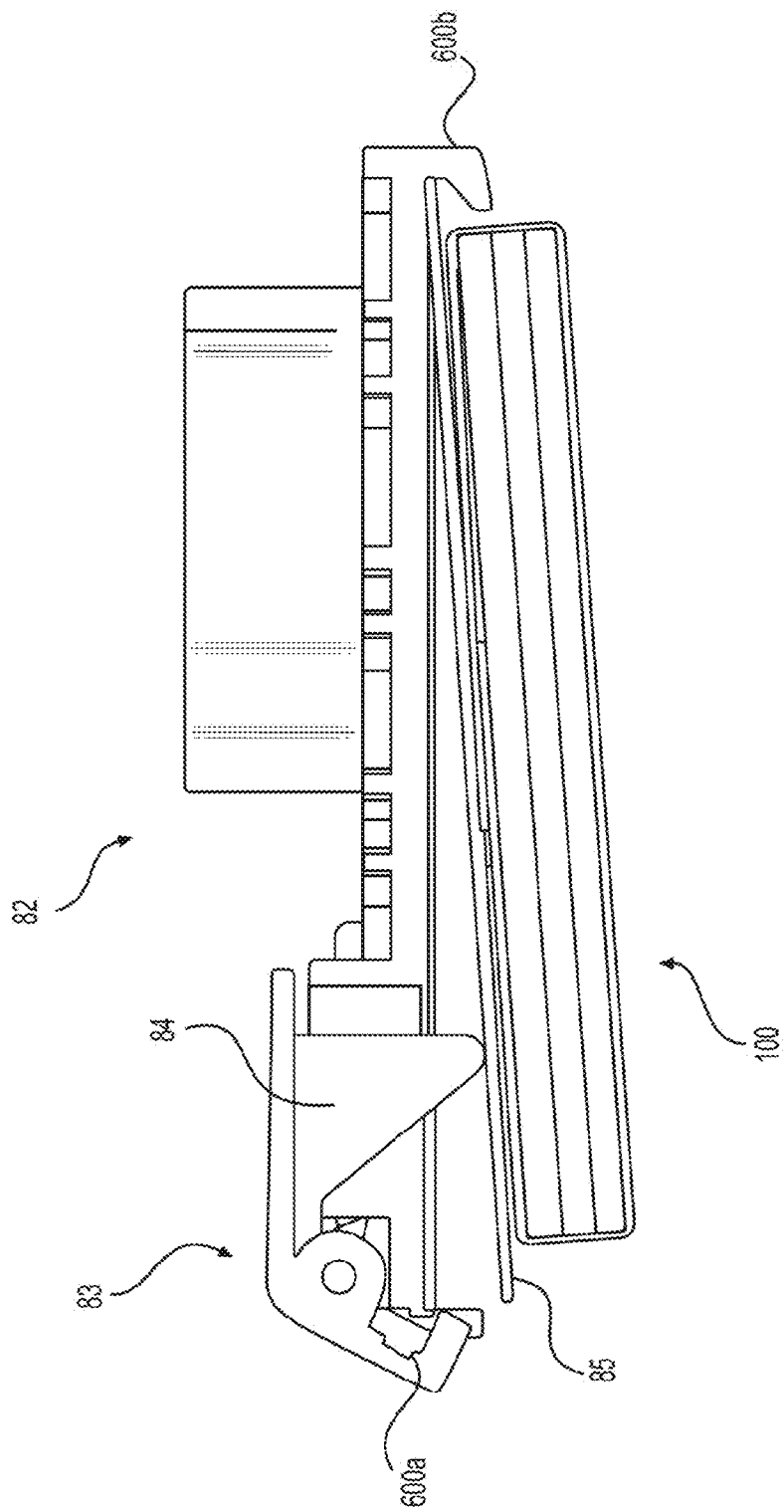
FIG. 8G is a cut away side view of an exemplary attachment mechanism for the pad as described herein in a release position.

FIGS. 8E-G demonstrate an exemplary release mechanism for the pad 100 as described herein. FIGS. 8A-8C show an embodiment of the pad 100 having a core of three airlaid layers 101, 102, 103 bonded and enclosed in a wrap layer 105 adhered to the top surface of the top airlaid layer 101. Additionally, the embodiment of FIGS. 8A-8C include a cardboard backing layer 85 adhered to the top surface of the pad 100. The cardboard backing layer 85 protrudes beyond the longitudinal edges of the pad 100 and the protruding longitudinal edges 86 of the cardboard backing layer 85 attach to the pad holder 82 of the robot 100. In one embodiment, the cardboard backing layer 85 is between 0.02" and 0.03" thick, between 68 and 72 mm wide and between 90-94 mm long. In one embodiment, the cardboard backing layer 85 is 0.026" thick, 70 mm wide and 92 mm long. In one embodiment, the cardboard backing layer 85 is coated on both sides with a water resistant coating, such as wax or polymer or a combination of water resistant materials, such as wax/polyvinyl alcohol, polyamine, and the cardboard backing layer 85 does not disintegrate when wetted.

In embodiments, the bottom surface 100b of the pad 100 may include one or more hair catching strips 100c for catch and collect loose hair during cleaning. In the embodiment of FIG. 9E, two hair catching strips 100c are depicted in dashed line to indicate the option nature of this feature. In an embodiment having one or more hair catching strips 100c, the strip or strips 100c may be located on outer longitudinal edges of the pad 100 or in a single strip on either longitudinal edge of the pad or down the middle of the pad. In embodiments, each hair catching strip 100c is less than 30% of the total surface area of the bottom surface 100b of the pad 100 and preferably is less than 20% of the surface area of the bottom surface 100b of the pad 100. The hair catching strip 100c may be a strip of material added to the wrap layer 105 that includes loose fibers with catching features, such as Velcro® hooks, rough edged fibers or fibers with a fused tip.

As shown in FIGS. 8E and 8G, the pad 100 as described herein can be secured to an autonomous robot through a pad holder 82 which can be attached to the robot 400. An exemplary pad release mechanism 83 is also shown in an up or pad-secure position. The pad release mechanism 83 includes a retainer 600a, or lip, that holds the pad 100 securely in place by grasping the protruding longitudinal edges 86 of the cardboard backing layer 85. In the version shown, the tip or end 84 of the pad release mechanism 83 includes a moveable retention clip 600a and an eject protrusion 84 that slides up through a slot or opening in the pad holder 82 when the pad is inserted into the holder 82, and is pushed into a down position to release the secured pad 100 as shown in FIG. 8G, as shown here pushing down on the attached backing layer 85, e.g. cardboard backing. The relationship between the pad and the pad holder 82 is also shown in a top view in FIG. 8F. In one embodiment, the pad release mechanism 83 is activated by a toggle button 477 located under the handle 419 of the robot 400, as shown in FIG. 4. The toggle motion is indicated by the dotted double arrow 478. Toggling the toggle button 477 moves a spring actuator that rotates the pad release mechanism 83, moving the retention clip 600a away from the cardboard backing layer 85 and moving the eject protrusion 84 through the slot in the the pad holder 882 so that the eject protrusion pushes the pad 100 out of the holder.

Returning to FIGS. 8A and 8B, in embodiments, the cardboard backing layer 85 may include cutouts 88 centered along the protruding longitudinal edges 86 of the cardboard backing layer 85 and corresponding in position with raised protrusion 94 on the bottom of the pad holder 82, as shown in FIG. 8D. In another embodiment, the cardboard backing layer 85 contains a first set of cutouts 88 centered on the protruding longitudinal edges 86 of the cardboard backing layer 85 and a second set of cutouts 90 on the lateral edges of the cardboard backing layer 85. The cutouts 88, 90 are symmetrically centered along the longitudinal center axis $PCA_{lon}$ of the pad 100 and lateral center axis $PCA_{lat}$ of the pad 100 and engage with corresponding protrusions 92, 94 centered on the longitudinal center axis $HCA_{lon}$ of the underside of the pad holder 82 and lateral center axis $PCA_{lat}$ on the underside of the pad holder 82. The pad holder 82 of the embodiment of FIG. 8D includes three raised protrusions 92, 94. This is so that a user may install the pad 100 in either of two identical directions (180 degrees opposite to one another) while allowing the pad holder 82 to more easily release the pad 100 when the release mechanism 83 is triggered. Other embodiments of the pad holder include four protrusions 92, 94 corresponding in position to the four cutouts 88, 90 on the cardboard backing layer in FIG. 8C. In still other embodiments, the pad holder 82 and pad 100 respectively include raised protrusions and corresponding cut outs in any other number or configuration for holding the pad in place and enabling selective release.

In FIG. 8D, the raised protrusion 94 on the longitudinal edge of the pad holder 82 is obscured by the retaining bracket 600a, which is shown in phantom view so that the raised protrusion 94 therebeneath is visible in the exemplary view. The protrusions 92, 94 both poke yoke attachment of the disposable pad 100 to the bottom of the pad holder 82 so that alignment if the pad 100 to the holder 82 is precise and retain the pad 100 relatively stationary to the pad holder 82 by preventing lateral and/or transverse slippage.

Because the cutouts 88, 90 extend into the surface area of the cardboard backing layer 85, they respectively interface with more lateral and longitudinal surface area of the raised protrusions 92, 94 and the pad is held in place against rotational forces as well by the cutout-protrusion retention system. The robot 100 moves in a scrubbing motion, as described above, and, in embodiments, the pad holder 82 oscillates the pad for additional scrubbing. In embodiments, the robot 400 oscillates the attached pad 100 in an orbit of 12-15 mm to scrub the floor 10 and applies 1 pound of downward pushing force or less to the pad. By aligning cutouts 88, 90 in the cardboard backing layer 85 with protrusions 92, 94, the pad 100 remains stationary relative to the holder during use, and the application of scrubbing motion, including oscillation motion, directly transfers from the pad holder 82 through the layers of the pad without loss of transferred movement.

In embodiments, the pad of FIGS. 1A-1D and 8A-8C are disposable pads. In other embodiments, the pad 100 is a reusable microfiber cloth pad having the same absorptive characteristics as those described herein with regard to embodiments. In embodiments having a washable, reusable microfiber cloth, the top surface of the cloth includes a secured stiff backing layer shaped and positioned like the cardboard backing layer of the embodiments of FIGS. 8A-8C. The stiff backing layer is made of heat resistant, washable material that can be machine dried without melting or degrading the backing. The stiff backing layer is dimensioned and has cutouts as described herein for interchangeable use with the embodiment of the pad holder 82 described with regard to the embodiments of FIGS. 8A-8G.

In other examples, the pad 100 is intended for use as a disposable dry cloth and comprises a single layer of needle punched spunbond or spunlace material having exposed fibers for entrapping hair. The dry pad 100 embodiment further comprises a chemical treatment that adds a tackiness characteristic to the pad 100 for retaining dirt and debris. In one embodiment, the chemical treatment is a material such as that marketed under the trade name DRAKESOL.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A floor cleaning robot comprising:
   a robot body;
   one or more drive wheels supporting the robot body above a floor surface and configured to maneuver the robot body across the floor surface;
   a pad holder disposed forward of the one or more drive wheels and configured to receive a cleaning pad;
   a fluid applicator to apply a fluid to the floor surface such that the received cleaning pad absorbs the fluid during forward movement of the robot body; and
   a controller to initiate operations of the fluid applicator to:
      apply sprays of the fluid at a first volumetric flow rate during a first spraying period to wet the floor surface, and
      apply sprays of the fluid at a second volumetric flow rate during a second spraying period to wet the floor surface, the second volumetric flow rate of the second spraying period being less than the first volumetric flow rate of the first spraying period, and the second spraying period being subsequent to the first spraying period.

2. The robot of claim 1, wherein the first volumetric flow rate is defined at least in part by:
   a distance travelled by the robot body between consecutive sprays of the fluid during the first spraying period, and
   a volume of the fluid in each of the consecutive sprays of the fluid during the first spraying period, wherein the distance is greater than a corresponding distance for the second volumetric flow rate or the volume is greater than a corresponding volume for the second volumetric flow rate.

3. The robot of claim 1, wherein the controller is configured to:
   during the first spraying period, initiate application of the sprays of the fluid at the first volumetric flow rate when the cleaning pad is dry to moisten the cleaning pad, and
   during the second spraying period, initiate application of the sprays of the fluid at the second volumetric flow rate when the moistened cleaning pad is absorptive.

4. The robot of claim 1, wherein the first spraying period has a length of time or is associated with a total travel distance, and the controller is configured to initiate application of the sprays of the fluid during the second spraying period after applying the sprays of the fluid during the first spraying period for the length of time or after causing the robot body to travel the total travel distance during the first spraying period.

5. The robot of claim 4, wherein the controller is configured to cause the robot body to move in birdsfoot movement patterns while applying the sprays of the fluid during the first spraying period.

6. The robot of claim 4, wherein the controller is configured to
   initiate application of a spray of the fluid each instance the robot body travels a first distance during the first spraying period, and
   initiate application of a spray of the fluid each instance the robot body travels a second distance during the second spraying period,
   wherein the first distance is less than the second distance.

7. The robot of claim 4, wherein the first spraying period has a duration between 1 and 3 minutes.

8. The robot of claim 4, wherein the first spraying period has a duration between 2 and 10 minutes.

9. The robot of claim 1, wherein the sprays of the fluid applied during the first spraying period each has a first volume, and the sprays of the fluid applied during the second spraying period each has a second volume, the first volume being larger than the second volume.

10. The robot of claim 9, wherein the first volume is about 1 mL, and the second volume is less than about 1 mL.

11. The robot of claim 1, wherein a first spray frequency is used to apply the fluid at the first volumetric flow rate and a second spray frequency is used to apply the fluid at the second volumetric flow rate, the first spray frequency being larger than the second spray frequency.

12. The robot of claim 1, wherein the controller is configured to initiate application of the sprays during the first spraying period at a start of a cleaning run.

13. The robot of claim 1, wherein the controller is configured, after the first spraying period, to apply the sprays during the second spraying period until an end of a cleaning run.

14. The robot of claim 1, wherein configurations of the controller to initiate the operations of the fluid applicator to apply the sprays of the fluid at the first volumetric flow rate comprise configurations of the controller to initiate operations of the fluid applicator to spray about 1 mL of the fluid every 30 to 60 centimeters travelled by the robot.

15. The robot of claim 1, wherein configurations of the controller to initiate the operations of the fluid applicator to apply the sprays of the fluid at the second volumetric flow rate comprise configurations of the controller to initiate operations of the fluid applicator to spray less than 1 mL of the fluid every 90 to 210 centimeters travelled by the robot.

16. The robot of claim 1, wherein the controller is configured to
navigate the robot to move across a first portion of the floor surface while the fluid applicator applies the sprays of the fluid to the first portion of the floor surface during the first spraying period, and
navigate the robot to move across a second portion of the floor surface while the fluid applicator applies the sprays of the fluid to the second portion of the floor surface during the second spraying period.

17. The robot of claim 1, wherein configurations of the controller to initiate the operations of the fluid applicator to apply the sprays of the fluid at the first volumetric flow rate comprise configurations of the controller to initiate operations of the fluid applicator at a start of a cleaning mission to apply the sprays of the fluid at the first volumetric flow rate.

18. The robot of claim 1, wherein the controller is configured to
initiate the operations of the fluid applicator to apply a spray of fluid on a portion of the floor surface during the first spraying period,
after the spray of fluid is applied to the portion of the floor surface, move the robot forward across the portion of the floor surface, and,
after moving the robot forward across the portion of the floor surface, move the robot backward across the portion of the floor surface.

19. The robot of claim 1, wherein the controller is configured to provide an alert to a user when the received cleaning pad is saturated.

20. The robot of claim 1, wherein the controller is configured to provide an alert to a user to instruct the user to refill a reservoir of the robot with fluid.

* * * * *

UNITED STATES PATENT AND TRADEMARK OFFICE
CERTIFICATE OF CORRECTION

PATENT NO. : 10,398,277 B2
APPLICATION NO. : 15/147661
DATED : September 3, 2019
INVENTOR(S) : Michael J. Dooley et al.

It is certified that error appears in the above-identified patent and that said Letters Patent is hereby corrected as shown below:

In the Specification

Column 1, Line 10, after "2013" insert -- , --.

Signed and Sealed this
Twelfth Day of November, 2019

Andrei Iancu
*Director of the United States Patent and Trademark Office*